US012788826B2

(12) United States Patent
Shin et al.

(10) Patent No.: US 12,788,826 B2
(45) Date of Patent: Nov. 10, 2026

(54) IMMUNOTHERAPY OF SKIN CANCER USING MPLA-LOADED HPG NANOPARTICLES

(71) Applicant: Yale University, New Haven, CT (US)

(72) Inventors: Kwangsoo Shin, New Haven, CT (US); Jungsoo Chang, New Haven, CT (US); W. Mark Saltzman, New Haven, CT (US); Michael Girardi, New Haven, CT (US)

(73) Assignee: Yale University, New Haven, CT (US)

( * ) Notice: Subject to any disclaimer, the term of this patent is extended or adjusted under 35 U.S.C. 154(b) by 457 days.

(21) Appl. No.: 18/314,688

(22) Filed: May 9, 2023

(65) Prior Publication Data

US 2023/0355801 A1 Nov. 9, 2023

Related U.S. Application Data

(60) Provisional application No. 63/339,811, filed on May 9, 2022.

(51) Int. Cl.

| | |
|---|---|
| ***A61K 47/69*** | (2017.01) |
| ***A61K 9/00*** | (2006.01) |
| ***A61K 9/127*** | (2006.01) |
| ***A61P 35/00*** | (2006.01) |

(52) U.S. Cl.

CPC ........ *A61K 47/6937* (2017.08); *A61K 9/0019* (2013.01); *A61K 9/127* (2013.01); *A61P 35/00* (2018.01)

(58) Field of Classification Search

None

See application file for complete search history.

(56) References Cited

U.S. PATENT DOCUMENTS

| | | | | |
|---|---|---|---|---|
| 4,596,576 | A | 6/1986 | De | |
| 5,354,742 | A | 10/1994 | Deming et al. | |
| 6,030,924 | A | 2/2000 | Mayer et al. | |
| 6,383,500 | B1 | 5/2002 | Wooley et al. | |
| 6,521,568 | B1 | 2/2003 | Kimura | |
| 8,206,747 | B2 | 6/2012 | Zale et al. | |
| 8,715,736 | B2 | 5/2014 | Sachdeva et al. | |
| 9,492,382 | B2 | 11/2016 | Türk et al. | |
| 9,492,400 | B2 | 11/2016 | Jon et al. | |
| 10,193,667 | B2 | 1/2019 | Park et al. | |
| 10,238,581 | B2 | 3/2019 | Deng et al. | |
| 10,272,019 | B2 | 4/2019 | Deng et al. | |
| 10,555,911 | B2 | 2/2020 | Zhou et al. | |
| 10,660,828 | B2 | 5/2020 | Deng et al. | |
| 10,758,459 | B2 | 9/2020 | Deng et al. | |
| 11,364,182 | B2 | 6/2022 | Deng et al. | |
| 11,826,438 | B2 | 11/2023 | Deng et al. | |
| 11,896,686 | B2 | 2/2024 | Deng et al. | |
| 11,918,695 | B2 | 3/2024 | Deng et al. | |
| 12,233,140 | B2 | 2/2025 | Deng et al. | |
| 2005/0019303 | A1 | 1/2005 | Tsai et al. | |
| 2005/0055078 | A1 | 3/2005 | Campbell | |
| 2006/0105026 | A1 | 5/2006 | Fortune et al. | |
| 2009/0155371 | A1 | 6/2009 | Sojka et al. | |
| 2009/0312402 | A1 | 12/2009 | Contag et al. | |
| 2011/0045092 | A1 | 2/2011 | Livney et al. | |
| 2011/0060036 | A1 | 3/2011 | Nie et al. | |
| 2011/0200666 | A1 | 8/2011 | Teichmueller et al. | |
| 2012/0195957 | A1 | 8/2012 | Sachdeva et al. | |
| 2013/0337066 | A1* | 12/2013 | Zhang | A61K 9/148 424/234.1 |
| 2014/0050803 | A1* | 2/2014 | Hernando | C12N 15/1137 514/19.2 |
| 2014/0093568 | A1* | 4/2014 | Bray | C12Q 1/6886 705/2 |
| 2016/0030349 | A1 | 2/2016 | Francis et al. | |
| 2017/0000037 | A1 | 1/2017 | Reijersen Van Buuren | |
| 2017/0266119 | A1 | 9/2017 | Deng | |
| 2018/0256480 | A1* | 9/2018 | Deng | A61Q 17/04 |
| 2018/0344655 | A1 | 12/2018 | Saltzman et al. | |
| 2024/0173216 | A1 | 5/2024 | Deng et al. | |
| 2024/0423972 | A1 | 12/2024 | Suh et al. | |
| 2025/0161295 | A1 | 5/2025 | Girardi et al. | |

(Continued)

FOREIGN PATENT DOCUMENTS

| | | | |
|---|---|---|---|
| EP | 2754684 | | 7/2014 |
| WO | 9702015 | A1 | 1/1997 |

(Continued)

OTHER PUBLICATIONS

International Search Report received for PCT Patent Application No. PCT/US2015/030169, mailed on Aug. 4, 2015, 4 pages.
International Search Report received for PCT Patent Application No. PCT/US2015/030187, mailed on Aug. 5, 2015, 4 pages.
International Search Report received for PCT Patent Application No. PCT/US2016/031879, mailed on Jul. 22, 2016, 4 pages.
International Search Report received for PCT Patent Application No. PCT/US2016/031890, mailed on Jul. 22, 2016, 5 pages.
International Search Report received for PCT Patent Application No. PCT/US2022/014676, mailed on May 2, 2022, 5 pages.
International Search Report received for PCT Patent Application No. PCT/US2023/018528, mailed on Jun. 23, 2023, 8 pages.
International Search Report received for PCT Patent Application No. PCT/US2023/018831, mailed on Aug. 9, 2023, 4 pages.
International Search Report received for PCT Patent Application No. PCT/US2023/079181, mailed on Feb. 27, 2024, 6 pages.
An, et al., "Preparation of monodisperse and size-controlled poly-(ethylene glycol) hydrogel nanoparticles using liposome templates", Journal of Colloid and Interface Science., vol. 331, No. 1, Mar. 1, 2009, pp. 98-103.

(Continued)

*Primary Examiner* — Celeste A Roney

(74) *Attorney, Agent, or Firm* — PABST PATENT GROUP LLP

(57) ABSTRACT

Encapsulation of MPLA in HPG-PLA nanoparticles having bioadhesive functional groups on the surface ("BNPs") prolongs the local antitumor immune response in melanoma and boosts the adaptive immune response conferred by MPLA due to the polymer's bioadhesive properties. Delivery of MPLA in BNP prolongs the host's antitumor response with lower quantities of MPLA. Studies in mice showed that NPs delivered intratumorally have good lymphatic drainage and accumulate in lymph nodes, with prolonged dendritic cell maturation in vivo with intratumoral delivery of BNP-MPLA compared to free MPLA and NNP-MPLA.

12 Claims, 17 Drawing Sheets

(56) References Cited

U.S. PATENT DOCUMENTS

| | | | |
|---|---|---|---|
| 2025/0248928 A1 | 8/2025 | Saltzman et al. |
| 2025/0295604 A1 | 9/2025 | Saltzman et al. |
| 2025/0345248 A1 | 11/2025 | Deng et al. |

FOREIGN PATENT DOCUMENTS

| | | | |
|---|---|---|---|
| WO | 2004103336 A2 | 12/2004 |
| WO | 2005002471 A1 | 1/2005 |
| WO | 2005089723 A1 | 9/2005 |
| WO | 2009066006 A1 | 5/2009 |
| WO | 2009123934 A2 | 10/2009 |
| WO | 2012151539 A2 | 11/2012 |
| WO | 2012156094 A1 | 11/2012 |
| WO | 2013064745 A1 | 5/2013 |
| WO | 2013149056 A1 | 10/2013 |
| WO | 2013166487 A1 | 11/2013 |
| WO | 2015172149 | 11/2015 |
| WO | 2015172153 | 11/2015 |
| WO | 2016176462 A1 | 11/2016 |
| WO | 2016183209 | 11/2016 |
| WO | 2016183217 A1 | 11/2016 |
| WO | 2019210134 A1 | 10/2019 |
| WO | 2020247653 A1 | 12/2020 |
| WO | 2021108722 A1 | 6/2021 |
| WO | 2022017508 A1 | 1/2022 |

OTHER PUBLICATIONS

Andreev , et al., "pH-sensitive membrane peptides (pHLIPs) as a novel class of delivery agents", Mol Membr Biol., vol. 27, No. 7, Oct. 13, 2010, pp. 341-352.

Artzi, et al., "Aldehyde-amine chemistry enables modulated bioseal-ants with tissue-specific adhesion", Adv Mater., vol. 21, Sep. 4, 2009, pp. 3399-3403.

Artzi, et al., "Aldehyde-Amine Chemistry Enables Tissue Adhesive Materials to Respond to Physiologic Variation and Pathologic States", Israel Journal of Chemistry, vol. 53, No. 9-10, Oct. 2013, pp. 748-755.

Bao, et al., "OX26 modified hyperbranched polyglycerol-conjugated poly(lactic-co-glycolic acid) nanoparticles: synthesis, characterization and evaluation of its brain delivery ability", J Mater Sci Mater Med., vol. 23, No. 8, Aug. 2012, pp. 1891-1901.

Beaudette, et al., "Development of Soluble Ester-Linked Aldehyde Polymers for Proteomics", Analytical Chemistry, vol. 83, No. 17, 2011, pp. 6500-6510.

Bergstrand, et al., "Interactions between pH-sensitive liposomes and model membranes", Biophys Chem., vol. 104, No. 1, May 1, 2003, pp. 361-379.

Blum, et al., "Prevention of K-Ras- and Pten-mediated intravaginal tumors by treatment with camptothecin-loaded PLGA nanoparticles", Drug Deliv Transl Res., vol. 1, No. 5., Oct. 1, 2011, pp. 383-394.

Carman, et al., "Adenosine Receptor Signaling Modulates Perme-ability of the Blood-Brain Barrier", The Journal of Neuroscience., vol. 31, No. 37, Sep. 14, 2011, pp. 13272-13280.

Charlton, et al., "Evaluation of bioadhesive polymers as delivery systems for nose to brain delivery: In vitro characterisation studies", Journal of Controlled Release, vol. 118, No. 2, May 2007, pp. 225-234.

Deng, et al., "A sunblock based on bioadhesive nanoparticles", Nat Mater., vol. 14, No. 12, Dec. 2015, pp. 1278-1285.

Deng, et al., "Improved i.p. drug delivery with bioadhesive nanoparticles", Proc Natl Acad Sci U S A., vol. 113, No. 41, Oct. 11, 2016, pp. 11453-11458.

Deng, et al., "The effect of hyperbranched polyglycerol coatings on drug delivery using degradable polymer nanoparticles", Biomateri-als, vol. 35, No. 24, Aug. 2014, pp. 6595-6602.

Feldborg, et al., "Quantitative Evaluation of Bioorthogonal Chem-istries for Surface Functionalization of Nanoparticles", Bioconjugate Chemistry, vol. 23, No. 12, 2012, pp. 2444-2450.

Fishman, et al., "Adenosine Receptors in Health and Disease", Handbook of Experimental Pharmacology., vol. 193, 2009, pp. 1-24 and 399-441.

Gao, et al., "Amphiphilic polylactic acid-hyperbranched polyglycerol nanoparticles as a controlled release system for poorly water-soluble drugs: physicochemical characterization", J Pharm Pharmacol., vol. 63, No. 6, Jun. 2011, pp. 757-764.

Gao, et al., "Overcoming the blood-brain barrier for delivering drugs into the brain by using adenosine receptor nanoagonist", ACS Nano., vol. 8, No. 4, 2014, pp. 3678-3689.

Gao, et al., "Synthesis and physicochemical characterization of a novel amphiphilic polylactic acid-hyperbranched polyglycerol con-jugate for protein delivery", Journal of Controlled Release, vol. 140, No. 2, Sep. 2009, pp. 141-147.

Heald, et al., "Poly(lactic acid)-Poly(ethylene oxide) (PLA-PEG) Nanoparticles: NMR Studies of the Central Solidlike PLA Core and the Liquid PEG Corona", Langmuir, vol. 18, No. 9, Mar. 23, 2002, pp. 3669-3675.

Iha, et al., "Applications of orthogonal "click" chemistries in the synthesis of functional soft materials", Chem Rev., vol. 109, No. 11, Nov. 2009, pp. 5620-5686.

Khang, et al., "Intrathecal delivery and its applications in leptomeningeal disease", Adv Drug Deliv Rev., vol. 186, No. 114338, Jul. 2022, 44 pages.

Khang, et al., "PLA-HPG Nanoparticles as a Therapeutic Carrier for Spinal Cord in Adult Mice", Database Compendex [Online], Engi-neering Information, Inc., New York, US, 2019, 1 page.

Koziara, et al., "Paclitaxel nanoparticles for the potential treatment of brain tumors", J Control Release, vol. 99, No. 2, Sep. 30, 2004, pp. 259-269.

Li, et al., "Methotrexate-conjugated and hyperbranched polyglycerol-grafted Fe3O4magnetic nanoparticles for targeted anticancer effects", European Journal of Pharmaceutical Sciences, Elsevier, Amster-dam, NL, vol. 48, No. 1, Oct. 26, 2012, pp. 111-120.

Li, et al., "Stealth nanoparticles: high density but sheddable PEG is a key for tumor targeting", J Control Release, vol. 145, No. 3, Aug. 3, 2010, pp. 178-181.

Liu, et al., "pH-sensitive nano-systems for drug delivery in cancer therapy", Biotechnol Adv., vol. 32, No. 4, 2014, pp. 693-710.

Mehdizadeh, et al., "Design Strategies and Applications of Tissue Bioadhesives", Macromol Biosci., vol. 13, No. 3, Mar. 2013, pp. 271-288.

Mohideen, et al., "Degradable bioadhesive nanoparticles for pro-longed intravaginal delivery and retention of elvitegravir", Biomateri-als, vol. 144, Nov. 2017, pp. 144-154.

Mugabe, et al., "In vivo Evaluation of Mucoadhesive Nanoparticulate Docetaxel for Intravesical Treatment of Non-Muscle-Invasive Blad-der Cancer", Clinical Cancer Research, vol. 17 No. 9, Feb. 28, 2011, pp. 2788-2798.

Mugabe, et al., "Paclitaxel incorporated in hydrophobically derivatized hyperbranched polyglycerols for intravesical bladder cancer therapy", BJU Int., vol. 103, No. 7, Apr. 2009, pp. 978-986.

Nag, et al., "Surface Engineering of Liposomes for Stealth Behav-ior", Pharmaceutics, vol. 5, No. 4, Oct. 25, 2013, pp. 542-569.

Nagasaki, et al., "The Reactive Polymeric Micelle Based on An Aldehyde-Ended Poly(ethylene glycol)/Poly(lactide) Block Copo-lymer", Macromolecules, vol. 31, No. 5, 1998, pp. 1473-1479.

Najar, et al., "Topical CpG enhances the response of murine malignant melanoma to dacarbazine", J Invest Dermatol., vol. 128, No. 9 ., Sep. 2008, pp. 2204-2210.

Romberg, et al., "Sheddable Coatings for Long-Circulating Nanoparticles", Pharmaceutical Research, vol. 25, 2008, pp. 55-71.

Saucier-Sawyer, et al., "Systemic Delivery of Blood-Brain Barrier Targeted Polymeric Nanoparticles Enhances Delivery to Brain Tissue", J Drug Target, vol. 23, No. 7-8, 2015, pp. 736-749.

Seo, et al., "Nanoparticle-mediated intratumoral inhibition of miR-21 for improved survival in glioblastoma", Biomaterials., vol. 201, 2019, pp. 87-98.

Solaro, et al., "Targeted Delivery of Protein Drugs by Nanocarri-ers", Materials., vol. 3, No. 3, 2010, pp. 1928-1980.

Suh, et al., "Biodegradable bioadhesive nanoparticle incorporation of broad-spectrum organic sunscreen agents", Bioeng Transl Med., vol. 4, No. 1, Jul. 6, 2018, pp. 129-140.

(56) References Cited

OTHER PUBLICATIONS

Suk, et al., "PEGylation as a strategy for improving nanoparticle-based drug and gene delivery", Advanced Drug Delivery Reviews, vol. 99, Part A, Apr. 1, 2016, pp. 28-51.
Vauthier, et al., "Poly(alkylcyanoacrylates) as biodegradable materials for biomedical applications", Adv Drug Deliv Rev., vol. 55, No. 4, Apr. 25, 2003, pp. 519-548.
Verschraegen, et al., "A phase II study of intravenous exatecan mesylate (DX-8951f) administered daily for 5 days every 3 weeks to patients with advanced ovarian, tubal or peritoneal cancer resistant to platinum, taxane and topotecan", Cancer Chemotherapy and Pharmacology, vol. 53, No. 1, Jan. 1, 2004, pp. 1-7.
Wiwatchaitawee, et al., "Enhancement of Therapies for Glioblastoma (GBM) Using Nanoparticle-based Delivery Systems", AAPS PharmSciTech, vol. 22, No. 2: 71, Feb. 11, 2021, 32 pages.
Zeng, et al., "Cholic acid-functionalized nanoparticles of star-shaped PLGA-vitamin E TPGS copolymer for docetaxel delivery to cervical cancer", Biomaterials., vol. 34, No. 25, Aug. 2013, pp. 6058-6067.
Zhou, et al., "Star-Shaped Amphiphilic Hyperbranched Polyglycerol Conjugated with Dendritic Poly(l-lysine) for the Codelivery of Docetaxel and MMP-9 siRNA in Cancer Therapy", ACS Appl Mater Interfaces, vol. 8, No. 20, May 25, 2016, pp. 12609-12619.
Aguado, M. T. and Lambert, P. H., "Controlled-release vaccines—biodegradable polylactide/ polyglycolide (PL/PG) microspheres as antigen vehicles", Immunobiology, 184(2-3): 113-25 (1992).
Bramwell, et al., "Particulate delivery systems for biodefense subunit vaccines," Adv. Drug Deliv. Rev. 57(9): 1247-65 (2005).
Hu, et al: "Nonsurgical treatment of skin cancer with local delivery of bioadhesive nanoparticles", Proceedings of the National Academy of Sciences, 118(7): (2021).
International Search Report for corresponding PCT/US2023/021557 dated Aug. 10, 2023.
Jiang, et al., "Biodegradable poly(lactic-co-glycolic acid) microparticles for injectable delivery of vaccine antigens", Adv. Drug Deliv. Rev., 57(3):391-410 (2005).
Qiu, H., "Nanomedicine approaches to improve cancer immunotherapy", Wiley Interdiscip Rev Nanomed Nanobiotechnology 9(5): e1456, (2017).
Yeh et al., "Self-Assembled Monothiol-Terminated Hyperbranched Polyglycerols on a Gold Surface: A Comparative Study on the Structure, Morphology, and Protein Adsorption Characteristics with Linear Poly(ethylene glycol)s", Langmuir, 24(9): 4907-16 (2008).
Yoshizaki, et al: "Potentiation of pH-sensitive polymer-modified liposomes with cationic lipid inclusion as antigen delivery carriers for cancer immunotherapy", Biomaterials, 35(28):8186-8196 (2014).
Zhang, et al: "Monophosphoryl lipid A-induced activation of plasmacytoid dendritic cells enhances the anti-cancer effects of anti-PD-LI antibodies", Cancer Immunology Immunotherapy, 70(3): 689-700 (2020).
Jia, et al., "Hyperbranched-hyperbranched polymeric nanoassembly to mediate controllable co-delivery of siRNA and drug for synergistic tumor therapy", Journal of Controlled Release, vol. 216, Oct. 28, 2015, pp. 9-17.

* cited by examiner

MPLA

• BMDC (bone marrow derived dendritic cells)
  • TNF-α from supernatant

Log Rank (Mantel-Cox) Test:

| | |
|---|---|
| Vehicle v free MPLA | p = 0.7229 |
| Vehicle v BNP MPLA | p = 0.0094 |
| Free MPLA vs. BNP MPLA | p = 0.0149 |

FIG. 12A
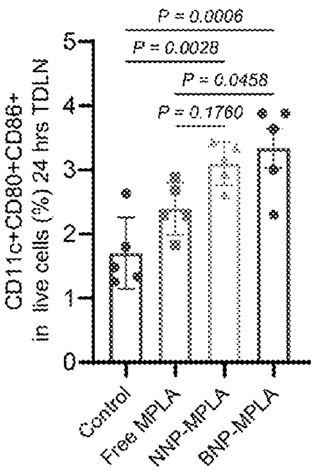
FIG. 12B
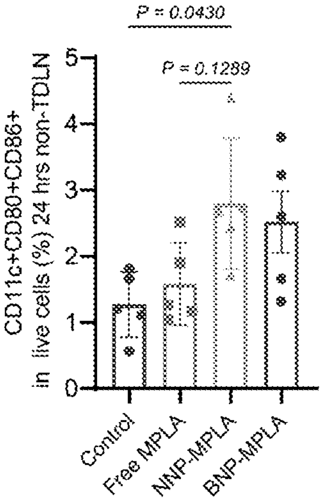
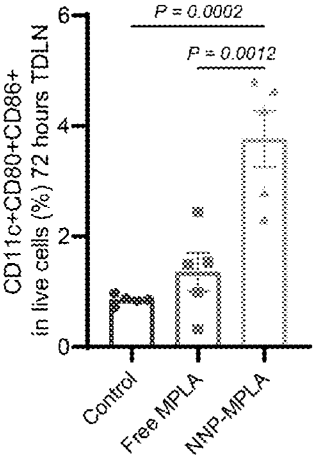
FIG. 12C

IMMUNOTHERAPY OF SKIN CANCER USING MPLA-LOADED HPG NANOPARTICLES

CROSS-REFERENCE TO RELATED APPLICATIONS

This application claims the benefit of and priority to U.S. Provisional Application No. 63/339,811 filed May 9, 2022, which is hereby incorporated by reference in its entirety.

STATEMENT REGARDING FEDERALLY SPONSORED RESEARCH OR DEVELOPMENT

This invention was made with government support under CA 121974 awarded by the National Institutes of Health. The government has certain rights in the invention.

FIELD OF THE INVENTION

This invention is generally in the field of immunomodulatory treatment of melanomas.

BACKGROUND OF THE INVENTION

Melanoma is a type of skin cancer that develops when melanocytes grow out of control. Melanoma is much less common than some other types of skin cancers, but more dangerous because it is much more likely to spread to other parts of the body if not caught and treated early.

Most skin cancers start in the top layer of skin, called the epidermis. There are three main types of cells in this layer: squamous cells: (flat cells in the outer part of the epidermis); basal cells (cells are in the lower part of the epidermis, constantly dividing to form new cells to replace the squamous cells that wear off); and melanocytes, which are pigmented cells that can become melanoma. The epidermis is separated from the deeper layers of skin by the basement membrane. When a skin cancer becomes more advanced, it generally grows through this barrier and into the deeper layers.

Based on the stage of the cancer and other factors, treatment options can include surgery; immunotherapy; targeted therapy drugs; chemotherapy; and radiation.

Targeted drugs only target parts of melanoma cells rather than standard chemotherapy drugs, which basically attack any quickly dividing cells. Most targeted drugs are used to treat melanomas that have certain gene changes such as BRAF gene changes. These represent approximately half of most melanomas. Drugs that target the BRAF protein (BRAF inhibitors) or the MEK proteins (MEK inhibitors) do not work on cells without an abnormal BRAF gene. Usually BRAF and MEK inhibitors are used in combination. BRAF inhibitors include vemurafenib (ZELBORAF®), dabrafenib (TAFINLAR®), and encorafenib (BRAFTOVI®). MEK inhibitors include trametinib (MEKINIST®), cobimetinib (COTELLIC®), and binimetinib (MEKTOVI®). Common side effects include skin thickening, rash, itching, sensitivity to the sun, headache, fever, joint pain, fatigue, hair loss, and nausea. Less common but serious side effects can include heart rhythm problems, liver problems, kidney failure, severe allergic reactions, severe skin or eye problems, bleeding, and increased blood sugar levels.

A small portion of melanomas have changes in the C-KIT gene that help them grow. Some targeted drugs, such as imatinib (GLEEVEC®) and nilotinib (TASIGNA®), can affect cells with changes in C-KIT.

Pembrolizumab (KEYTRUDA®) and nivolumab (OPDIVO®) target PD-1, a protein on T cells that normally help keep these cells from attacking other cells in the body. By blocking PD-1, these drugs boost the immune response against melanoma cells. Atezolizumab (TECENTRIQ®) is a drug that targets PD-L1, a protein related to PD-1 that is found on some tumor cells and immune cells. Blocking this protein can help boost the immune response against melanoma cells. Ipilimumab (YERVOY®) is another drug that boosts the immune response, by blocking CTLA-4.

Relatlimab targets LAG-3, another checkpoint protein on certain immune cells that normally helps keep the immune system in check. This drug is given along with the PD-1 inhibitor nivolumab (in a combination known as OPDUALAG®).

Immunostimulants are also used. For example, interleukins boost the immune system in a general way and are sometimes used to treat melanoma. Bacille Calmette-Guerin (BCG) vaccine activates the immune system and can sometimes help treat stage III melanoma. Imiquimod (ZYCLARA®) stimulates a local immune response against skin cancer cells. Unfortunately, immunomodulators, while safe and somewhat efficacious, are limited by short therapeutic effect and nonspecific delivery.

It is therefore an object of the present invention to provide an immunostimulant useful for treatment of cancers, such as melanoma, which is safe, efficacious, and provides a more prolonged therapy.

SUMMARY OF THE INVENTION

Monophosphoryl lipid A (MPLA), while a safe and effective immunomodulator, is ineffective on its own for antitumor immunity and effect. However, encapsulation of MPLA in hyperbranched polyglycerol-polylactide (HPG-PLA) nanoparticles having bioadhesive functional groups on the surface (bioadhesive nanoparticles, "BNPs") prolongs the local antitumor immune response in melanoma and boosts the adaptive immune response conferred by MPLA due to the polymer's bioadhesive properties. Delivery of MPLA in BNP prolongs the host's antitumor response with lower quantities of MPLA.

Examples demonstrate sodium cholate (CHA)-assisted single emulsion solvent evaporation method can produce small MPLA loaded PLA-HPG NPs maintaining NP-surface with HPG. BNP-MPLA show higher induction of dendritic cell (DC) maturation compared to free MPLA, and comparable DC maturation to lipopolysaccharide (LPS).

Studies in mice showed that NNP-MPLA and BNP-MPLA yielded higher percentages of CD11c and MHCII+ cells. At 48 hours after incubation of the BMDCs with the particles, BNP-MPLAs induced a higher percentage maturation of dendritic cells compared to the MPLA and NNP-MPLA. NPs delivered intratumorally have good lymphatic drainage and accumulate in lymph nodes, with prolonged dendritic cell maturation in vivo with intratumoral delivery of BNP-MPLA compared to free MPLA and NNP-MPLA. The evidence in vitro and in vivo shows tumor regression of melanoma model with BNP-MPLA.

BRIEF DESCRIPTION OF THE DRAWINGS

*Nanomed Nanobiotechnology* 9, (2017).

FIG. 7C is a comparison focusing on levels of TNF-alpha in MPLA, NNP-MPLA, and BNP-MPLA after 48 hours incubation.

FIGS. 12A-12C are graphs showing the amount of activation of immune cells in vivo in tumor draining lymph nodes (TDLNs) with MPLA is increased with nanoparticle encapsulation. FIG. 12A shows activation of BMDCs after single intratumoral injection in TDLN and non-TDLN with corresponding quantification of BMDCs maturation (n=5). FIG. 12B shows results for CD80 and CD86 in live CD11c+ cells in non-TDLNs after a single injection at 24 h with corresponding quantification of BMDCs maturation in non-TDLN (n=5). In both the TDLN and non-TDLN, there is a significant dendritic cell maturation in vivo with NNP or BNP-MPLA compared to the free MPLA. FIG. 12C shows results for activation of BMDCs in TDLNs after 72 h after a single injection, demonstrating that NNP-MPLA prolongs the dendritic cell maturation compared to free MPLA.

FIG. 13A show corresponding quantification of CD68+ cells in TDLN 72 h after injection (n=5). FIG. 13B show corresponding quantification of CD68+ cells in TDLN 5 days after injection (n=5). Statistical significance between different groups was obtained by one-way t-test. Data are means±SD. DC: dendritic cells, TDLN: tumor draining lymph node.

FIG. 14A shows quantification of NK expression in live CD45+CD3+ cells in the tumors. (n=5). FIG. 14B shows quantification of Tregs in the tumors with significantly decreased Treg population in NNP-MPLA treated tumors in comparison to the control and free MPLA. FIG. 14C shows quantification of CD8/Treg ratio in the tumors. There was a significantly increased CD8 to Treg ratio in tumors treated with NNP-MPLA indicating a higher cytotoxic T cell population with NNP-MPLA treatment compared to both control and free MPLA. FIG. 14D shows quantification of interferon in serum from mice at various time points after a single treatment injection. There was a notable increase in cytokine production in the NNP-MPLA treated groups; at 24 hr, the detectable IFN-γ were similar across groups, however there was a sustained increase in IFN-γ detected in serum in NNP-MPLA injected mice after 72 hr, and finally, significantly increased IFN-γ at 5 days after NNP-MPLA injection compared to control and free MPLA.

FIG. 15A shows there was a significant delay in tumor growth with NNP-MPLA and chemotherapy SBI-111. Growth curves are shown for tumors injected with a single treatment of NNP-MPLA or SBI-111 or combination SBI-111 and NNP-MPLA. FIG. 15B shows the weight change in treated mice. A single treatment and the combination treatment was well tolerated in mice as evidenced by only a slight weight change of mice on the day after treatment. FIG. 15D shows the survival curve of mice after a single treatment with either NNP-MPLA, SBI-111, or SBI-111 and NNP-MPLA. (n=9-10). Data are means±SEM. Statistical significance was calculated by one-way ANOVA and Mantel-Cox test. *P<0.001, P<0.01, and *P<0.05

FIG. 16A shows the combined growth curve for tumors injected with a single treatment of free MPLA, NNP-MPLA, SBI-111, or combination chemoimmunotherapy with free MPLA or NNP-MPLA. (n=7-8). The combination of chemotherapy with NNP-MPLA demonstrated a stark slowing in tumor growth. FIG. 16B shows the mouse weight changes after treatment injection (n=6-8). FIG. 16C show the tumor weight at harvest, 14 days after single treatment (n=6-8). Data are means±SEM. Statistical significance was calculated by one-way ANOVA and Mantel-Cox test. *P<0.001, P<0.01, and *P<0.05.

DETAILED DESCRIPTION OF THE INVENTION

I. Definitions

Figure 1A:
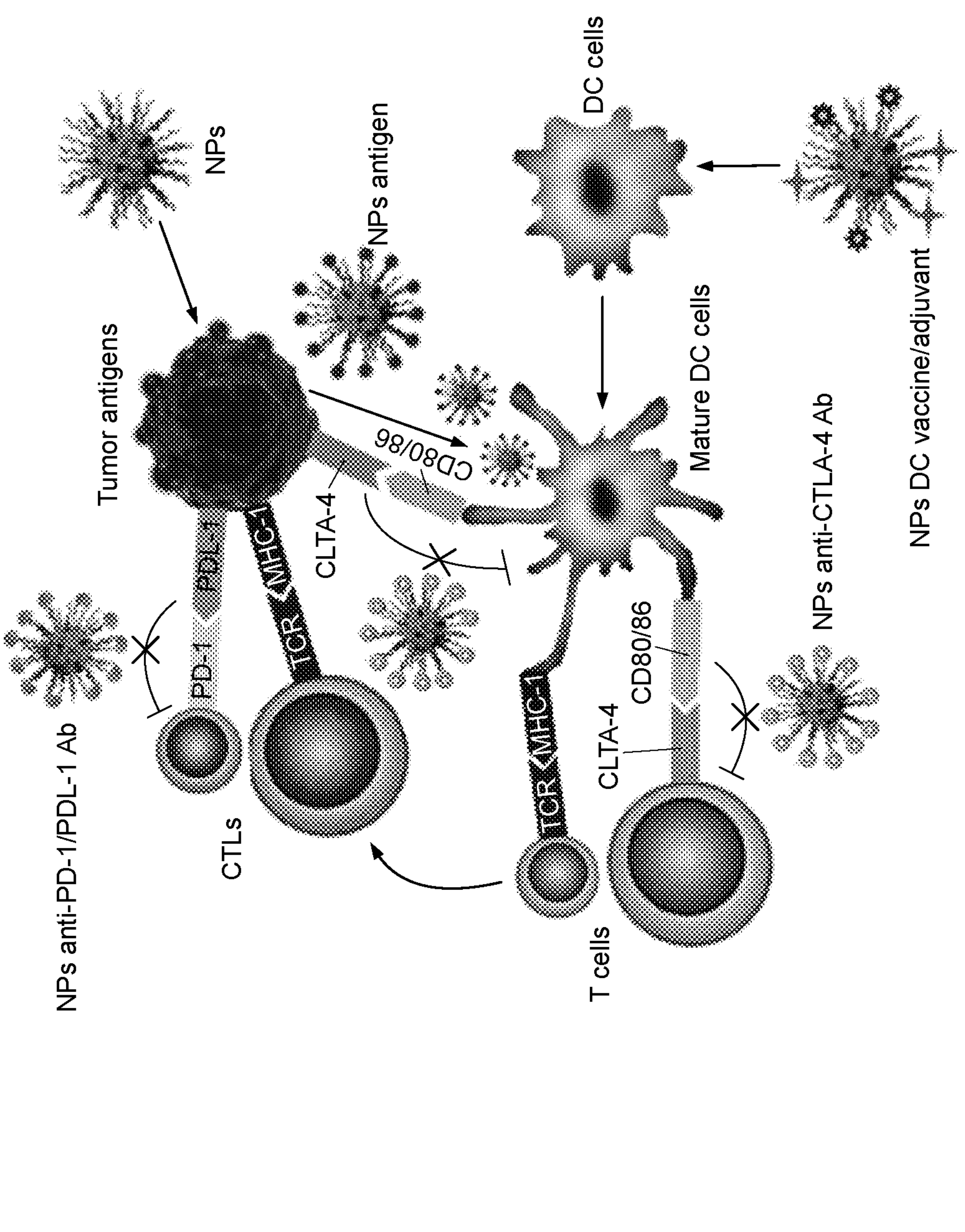
FIG. 1A is schematic of NP based immunotherapy, demonstrating the various routes to increasing the immune response. Diagram from Qiu, H., Min, Y., Rodgers, Z., Zhang, L. & Wang, A. Z. Nanomedicine approaches to improve cancer immunotherapy. *Wiley Interdiscip Rev*

"Nanoparticle," as used herein, generally refers to a nanoparticle of any shape having a diameter from about 1 nm up to, but not including, about 1 micron, more preferably from about 5 nm to about 500 nm, most preferably from about 5 nm to about 100 nm. Nanoparticles having a spherical shape are generally referred to as "nanospheres".

"Mean nanoparticle size," as used herein, generally refers to the statistical mean nanoparticle size (diameter) of the nanoparticles in a population of nanoparticles. The diameter of an essentially spherical nanoparticle may be referred to as the physical or hydrodynamic diameter. The diameter of a non-spherical nanoparticle may refer preferentially to the hydrodynamic diameter. As used herein, the diameter of a non-spherical nanoparticle may refer to the largest linear distance between two points on the surface of the nanoparticle. Mean nanoparticle size can be measured using methods known in the art, such as dynamic light scattering.

"Monodisperse" and "homogeneous size distribution," are used interchangeably herein and describe a plurality of nanoparticles where the nanoparticles have the same or nearly the same diameter or aerodynamic diameter. As used herein, a monodisperse distribution refers to nanoparticle distributions in which 80 to 95%, or an integer therebetween or greater of the distribution lies within 5% of the mass median diameter or aerodynamic diameter.

"Hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

"Hydrophobic" as used herein refers to substances that lack an affinity for water; tending to repel and not absorb water as well as not dissolve in or mix with water.

As used herein, an amphiphilic polymer is one which has one end formed of a hydrophilic polymer and one end formed of a hydrophobic polymer. As a result, when dispersed into a mixture of water and low water-solubility solvent such as many of the organic solvents, the hydrophilic end orients into the water and the hydrophobic end orients into the low water-solubility end.

Self-assembling refers to the use of amphiphilic polymers, alone or in mixture with hydrophilic and/or hydrophobic polymers, which orient in a mixture of aqueous and non-aqueous solvents to form nanoparticles, wherein the hydrophilic ends orient with the other hydrophilic ends and the hydrophobic ends orient with the other hydrophobic ends.

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions. The term "therapeutic or prophylactic agent" refers to an agent that can be administered to prevent or treat one or more symptoms of a disease or disorder. Therapeutic agents can be a nucleic acid, a nucleic acid analog, a small molecule (less than 2000 D, less than 1500 D or less than 1000 D), a peptidomimetic, a protein, peptide, carbohydrate or sugar, lipid, or surfactant, or a combination thereof.

"Effective amount" or "therapeutically effective amount", as used herein, refers to an amount of drug effective to alleviate, delay onset of, or prevent one or more symptoms of a disease or disorder. The terms "treating" or "preventing", as used herein, can include preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

"Pharmaceutically acceptable," as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

"Biocompatible" and "biologically compatible," as used herein, generally refer to materials that are, along with any metabolites or degradation products thereof, generally nontoxic to the recipient, and do not cause any significant adverse effects to the recipient. Generally, biocompatible materials are materials which do not elicit a significant inflammatory or immune response when administered to a patient.

"Biodegradable" as used herein means that the materials degrade or break down into its component subunits, or digestion, e.g., by a biochemical process, of the material into smaller (e.g., non-polymeric) subunits.

II. Nanoparticle Formulations

A. HPG-PLA Nanoparticles

The nanoparticles contain a core and a shell or coating. The shell is formed of hyperbranched polyglycerol (HPG). The HPG is covalently bound to hydrophobic polymer that form the core, such that the hydrophilic HPG is oriented towards the outside of the nanoparticles and the hydrophobic polymer is oriented to form the core.

The HPG coating can be modified to adjust the properties of the nanoparticles. For example, unmodified HPG coatings impart stealthy properties to the nanoparticles which resist non-specific protein absorption and are referred to as non-bioadhesive nanoparticles (NNPs). As used herein, the hydroxyl groups or other groups on the HPG coating are chemically modified to form functional groups that react with functional groups on tissue or otherwise interact with tissue to adhere the nanoparticles to the tissue, cells, or extracellular materials, such as proteins. Such functional groups include aldehydes, amines, oximes, and O-substituted oximes, most preferably aldehydes. Nanoparticles with an HPG coating chemically modified to form functional groups are referred to as bioadhesive nanoparticles (BNPs). The chemically modified HPG coating of BNPs forms a bio-adhesive corona of the nanoparticle surrounding the hydrophobic polymer forming the core. See, for example, WO 2015/172149, WO 2015/172153, WO 2016/183209, and U.S. Published Applications 2017/0000737 and 2017/0266119.

The core of the NPs preferably is formed of polymers fabricated from polylactides (PLA) and copolymers of lactide and glycolide (PLGA). These have established commercial use in humans and have a long safety record (Jiang, et al., Adv. Drug Deliv. Rev., 57(3):391-410); Aguado and Lambert, Immunobiology, 184(2-3):113-25 (1992); Bramwell, et al., Adv. Drug Deliv. Rev., 57(9):1247-65 (2005)).

Hyperbranched polyglycerol (HPG) is a highly branched polyol containing a polyether scaffold. Hyperbranched polyglycerol can be prepared using techniques known in the art. It can be formed from controlled etherification of glycerol via cationic or anionic ring opening multi-branching polymerization of glycidol. For example, an initiator having multiple reactive sites is reacted with glycidol in the presence of a base to form hyperbranched polyglycerol (HPG). Suitable initiators include, but are not limited to, polyols, e.g., triols, tetraols, pentaols, or greater and polyamines, e.g., triamines, tetraamines, pentaamines, etc. In one embodiment, the initiator is 1,1,1-trihydroxymethyl propane (THP).

A formula for hyperbranched polyglycerol as described in EP 2754684 is

Formula I

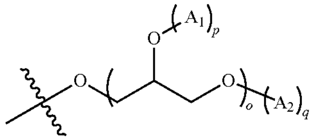

wherein o, p and q are independently integers from 1-100, and wherein A1 and A2 are independently Formula II

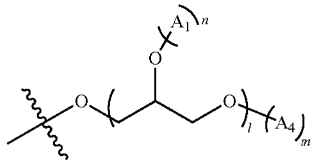

wherein l, m and n are independently integers from 1-100, and wherein A3 and A4 are defined as A1 and A2, with the proviso that A3 and A4 are hydrogen, n and m are each 1 for terminal residues.

The surface properties of the HPG can be adjusted based on the chemistry of vicinal diols. For example, the surface properties can be tuned to provide stealth nanoparticles, i.e., nanoparticles that are not cleared by the MPS due to the presence of the hydroxyl groups; adhesive (sticky) nanoparticles, i.e., nanoparticles that adhere to the surface of tissues, for example, due to the presence of one or more reactive functional groups, such as aldehydes, amines, oxime, or O-substituted oxime that can be prepared from the vicinal hydroxyl moieties; or targeting by the introduction of one or more targeting moieties which can be conjugated directly or indirectly to the vicinal hydroxyl moieties. Indirectly refers to transformation of the hydroxy groups to reactive functional groups that can react with functional groups on molecules to be attached to the surface, such as active agents and/or targeting moieties, etc.

The hyperbranched nature of the polyglycerol allows for a much higher density of hydroxyl groups, reactive functional groups, and/or targeting moieties than obtained with linear polyethylene glycol. For example, the nanoparticles can have a density of surface functionality (e.g., hydroxyl groups, reactive functional groups, and/or targeting moieties) of at least about 1, 2, 3, 4, 5, 6, 7, or 8 groups/nm2.

The molecular weight of the HPG can vary. For example, in those embodiments wherein the HPG is covalently attached to the materials or polymers that form the core, the molecular weight can vary depending on the molecular weight and/or hydrophobicity of the core materials. The molecular weight of the HPG is generally from between about 1,000 and about 1,000,000 Daltons, from about 1,000 to about 500,000 Daltons, from about 1,000 to about 250,000 Daltons, or from about 1,000 to about 100,000 Daltons. In those embodiments wherein the HPG is covalently bound to the core materials, the weight percent of HPG of the copolymer is from about 1% to about 50%, such as about 1, 2, 3, 4, 5, 10, 15, 20, 25, 30, 35, 40, 45 or 50%.

In some embodiments, the HPG is covalently coupled to a hydrophobic material or a more hydrophobic material, such as a polymer. Upon self-assembly, nanoparticles are formed containing a core containing the hydrophobic material and a shell or coating of HPG. HPG coupled to the polymer PLA is shown below:

Formula III

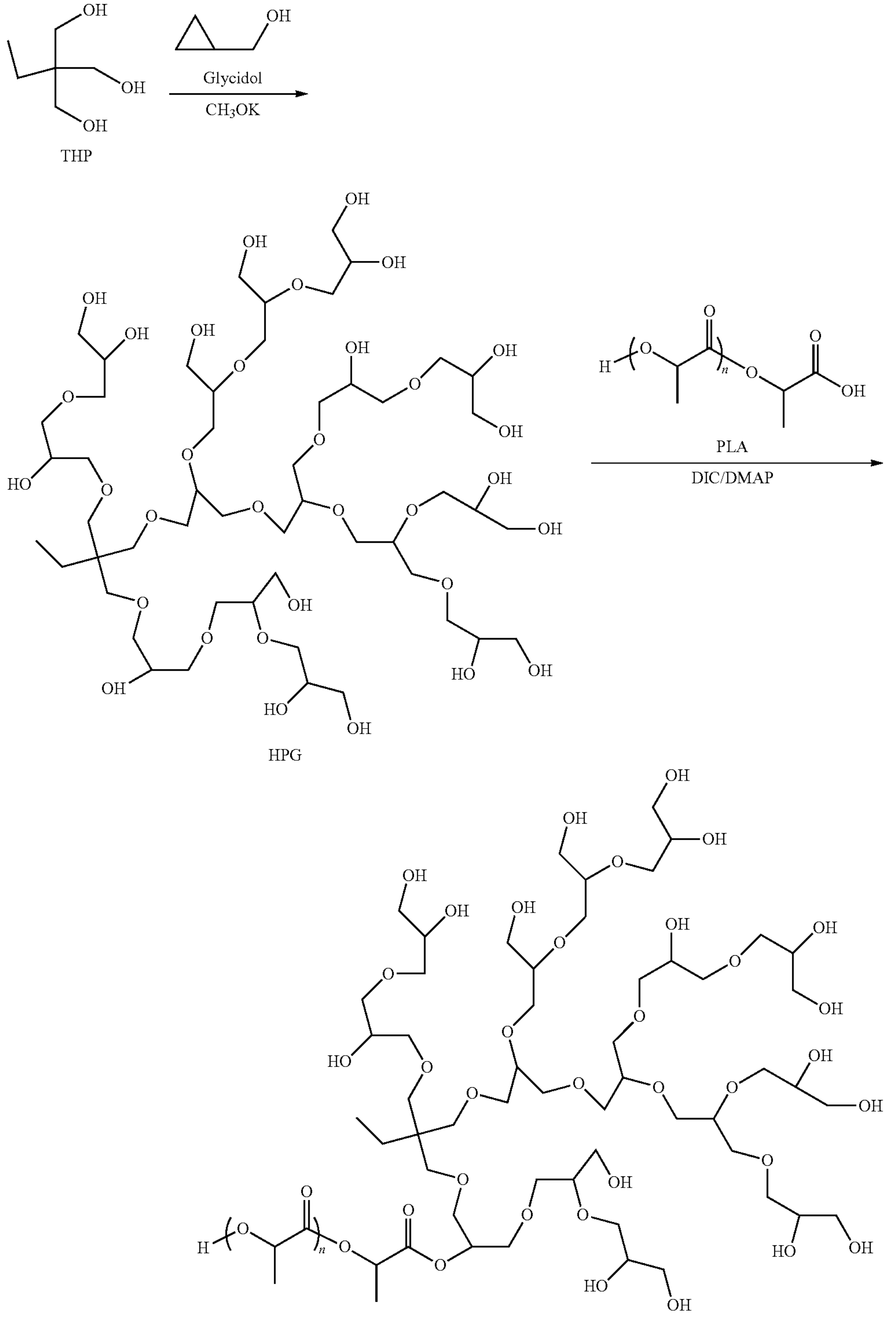

THP

HPG

PLA-HPG

HPG-coated nanoparticles can be modified by covalently attaching PEG to the surface. This can be achieved by converting the vicinyl diol groups to aldehydes and then reacting the aldehydes with functional groups on PEG, such as aliphatic amines, aromatic amines, hydrazines and thiols. The linker has end groups such as aliphatic amines, aromatic amines, hydrazines, thiols and O-substituted oxyamines. The bond inserted in the linker can be disulfide, orthoester and peptides sensitive to proteases.

PEG with a functional group or a linker can form a bond with aldehyde on PLA-HPG-CHO and reversed the bioadhesive state of PLA-HPG-CHO to stealth state. This bond or the linker is labile to pH change or high concentration of peptides, proteins and other biomolecules. After administration systematically or locally, the bond attaching the PEG to PLA-HPG-CHO can be reversed or cleaved to release the PEG in response to environment, and expose the bioadhesive PLA-HPG-CHO nanoparticles to the environment. Subsequently, the nanoparticles will interact with the tissue and attach the nanoparticles to the tissues or extracellular materials such as proteins. The environment can be acidic environment in tumors, reducing environment in tumors, protein rich environment in tissues.

HPG can be covalently bound to polymer that form the core of the nanoparticles using methodologies known in the art. For example, an HPG such as HPG can be covalently coupled to a polymer having carboxylic acid groups, such as PLA, PGA, or PLGA using DIC/DMAP.

The HPG can be initiated from hydroxyl, amine, and carboxylate terminated molecules, such as an alcohol with one or multiple long hydrophobic tail. In another example, the HP, such as HPG, can be initiated from special functionalized initiators to facilitate the conjugation to more materials. These special initiators include disulfide (Yeh et al., Langmuir. 24(9):4907-16(2008)).

The HPG can be functionalized to introduce one or more reactive functional groups that alter the surface properties of the nanoparticles. The surface of the nanoparticles can further be modified with one or more targeting moieties or covalently bound to an HPG such as HPG via a coupling agent or spacer in organic such as dichloromethane (DCM), dimethylformamide (DMF), dimethyl sulfoxide (DMSO), tetrahydrofuran (THF), diisopropylcarbodiimide (DIC), 4-(N,N-dimethylamino)pyridine (DMAP), dicyclohexylcarbodiimide (DCC), DIC/DMAP, DCC/DMAP, Acylchloride/pyridine. In some embodiments, the polymer is functionalized/modified before nanoparticle formation.

HPG coated NPs can be transformed to aldehyde terminated NPs by NaIO4 treatment (or carboxylic acid terminated by NaIO4 treatment followed by sodium chlorite treatment) so the targeting moieties may be directly covalently attached to NPs via aldehyde (or carboxylic acid) groups on NPs and functional groups (amine, hydrazine, amino-oxy and their derivatives) on the targeting moieties or indirectly attached to the NPs via coupling agents or spacers (such as amino-oxy modified biotin and cysteine).

Since high molecular weight HPG has better resistance to non-specific adsorption to biomolecules, the low molecular weight components can be removed from the synthesized HPG by multiple solvent precipitations and dialysis.

In the preferred embodiment, a polyhydroxy acid such as PLA is selected as the hydrophobic core material because it is biodegradable and has a long history of clinical use. To covalently attach the PLA to HPG, one can first functionalize the HPG with an amine and then conjugate the carboxylic group on PLA to the amine. This approach is efficient but cannot be used to make HPG as surface coatings since any amines that do not react with PLA will lead to a net positive charge on the neutral HPG surface and reduce the ability of HPG to resist adsorption of other molecules on the surface. To avoid this, a one-step esterification between PLA and HPG can be employed, which maintains the charge neutral state of the HPG. Alternatively, PLGA can be used as the hydrophobic core material for covalent attachment to HPG.

PLA-HPG NPs can be "non-adhesive" ("NNP") or bioadhesive ("BNP") based on the functional groups on the surface thereof.

The following is a structural formula of a NNP.

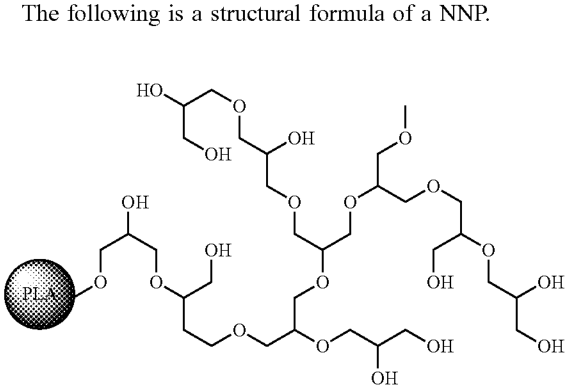

The following is a structural formula of a BNP.

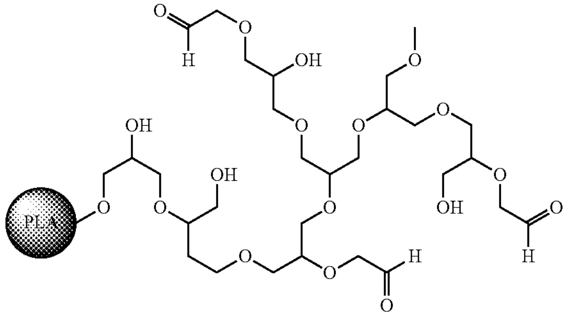

BNP

The NNP are "stealthy" (non-adhesive) and colloidally stable.

The BNP are bioadhesive, moderately stable, have longer retention at the site of administration and delayed but enhanced cellular internalization, as compared to NNP. BNPs are preferred for prolonged retention of immune agonists and anti-tumor immune responses.

The NNP and BNP are considered to be "self-assembling" and can encapsulate agent at the time of formulation. Methods of forming NNP or BNP encapsulating an immune modulator such as MPLA including:

Solubilizing MPLA in dichloromethane ("DCM") in combination with methanol ("MeOH") or CM+MeOH or dimethyl sulfoxide ("DMSO"), with triethanolamine ("TEA") (0.2 wt %), then using a single emulsion method such as ethyl acetate ("EA") to produce NPs having a size between about 100 and 150 nm but no MPLA encapsulation; DCM and DMSO, producing NPs between about 180 and 250 nm; and co-solvent CDM/ethyl acetate ("EA") to produce NPs of about 300 nm in diameter.

Nanoprecipitation using DMSO to produce PLA-HPG precipitates and forming NPs, before precipitation of MPLA, where NPs and MPLA aggregates are formed separately, or a surfactant-assisted emulsion method, which is preferred.

A surfactant-assisted emulsion method using polyvinyl alcohol ("PVA") shields PEG or HPG surface on NPs so they can lose their "stealthy" or "bioadhesive" properties.

A surfactant-assisted emulsion method using PLURONIC (F68, F127) or Polysorbate 80, provides additional stealth properties.

Sodium cholate ("CHA") provides negative charges, its small molecule, and little interference on surface polymers.

After BNP conversion, aldehyde-HPG reduces colloidal stability of NPs. Surfactants contributed to colloidal stability of NPs.

B. Immunostimulants to be Encapsulated or Attached to the Surface of the Nanoparticles Immunostimulants are delivered in or as part of the NPs. In a preferred embodiment the immunostimulant is MPLA.

Figure 2A:
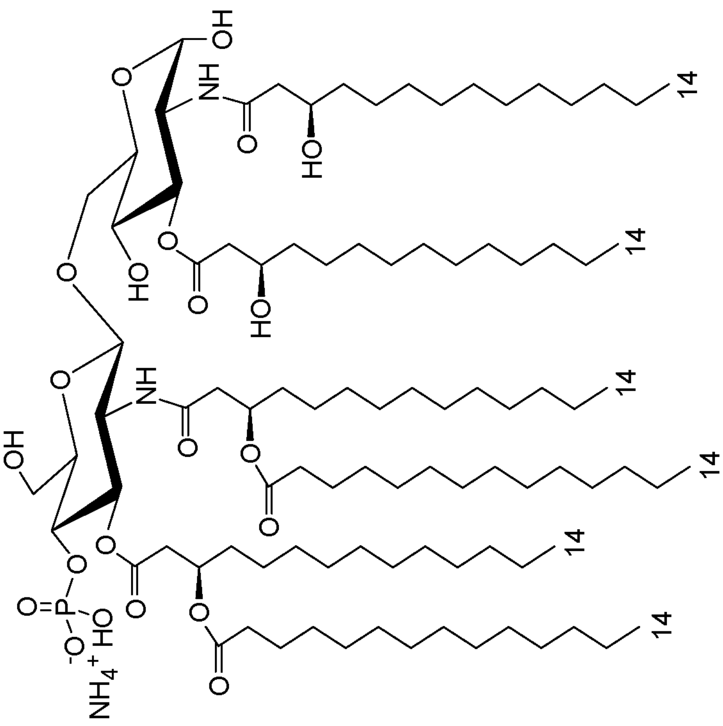
FIGS. 2A-2C are schematics of MPLA (FIG. 2A); the lipopolysaccharide ("LPS") component thereof (FIG. 2B) and the immune pathway it initiates (FIG. 2C).
Figure 2B:
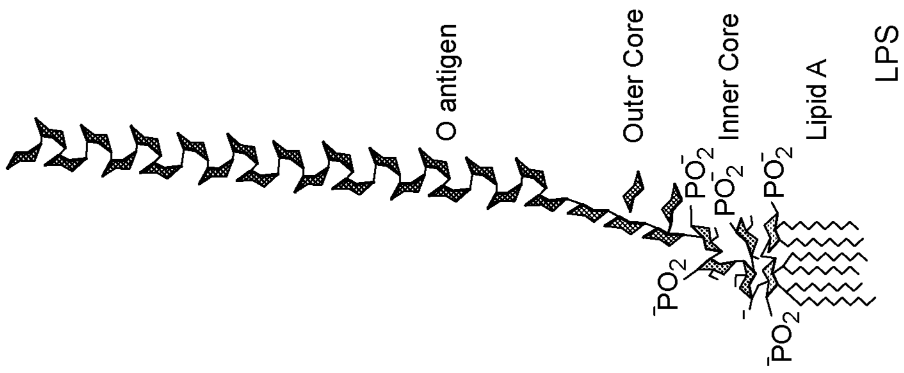
Figure 2C:
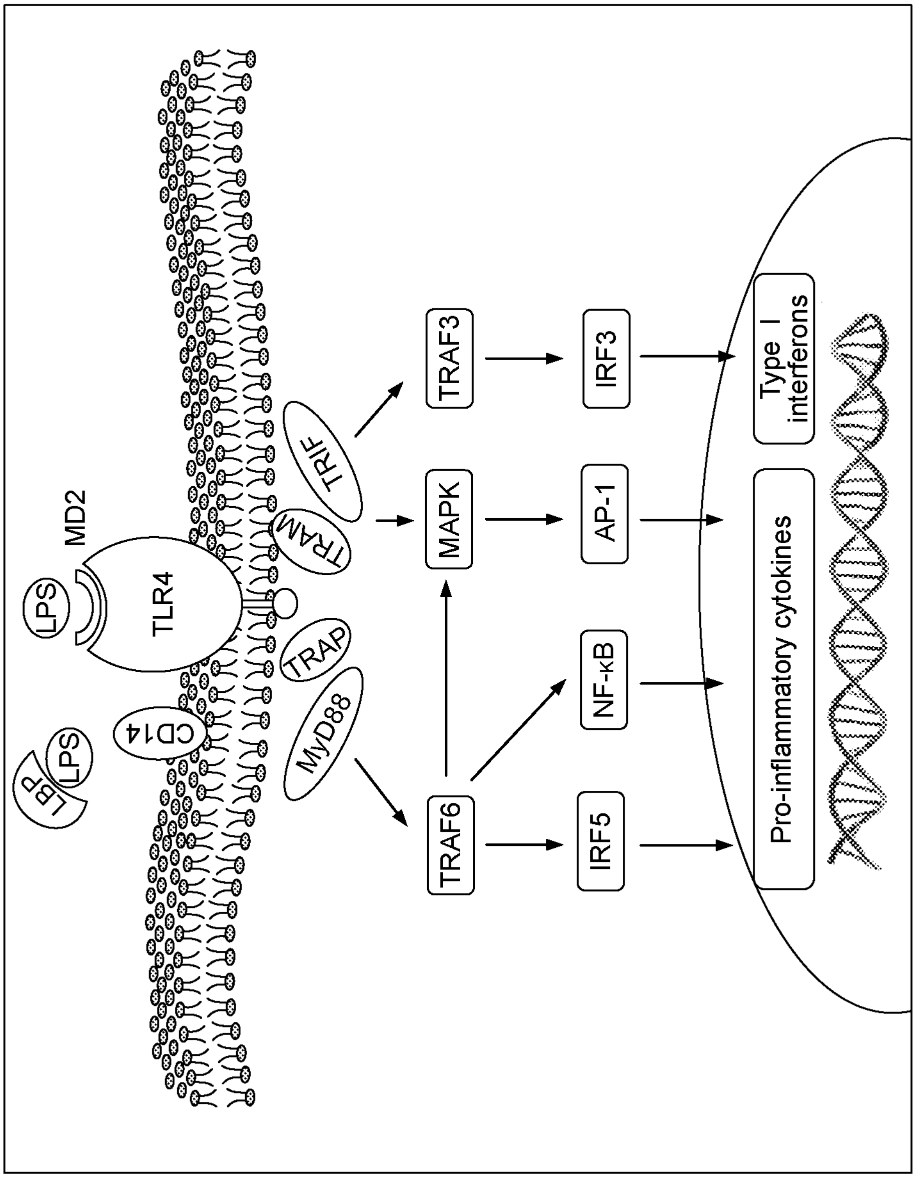
Figure 3:
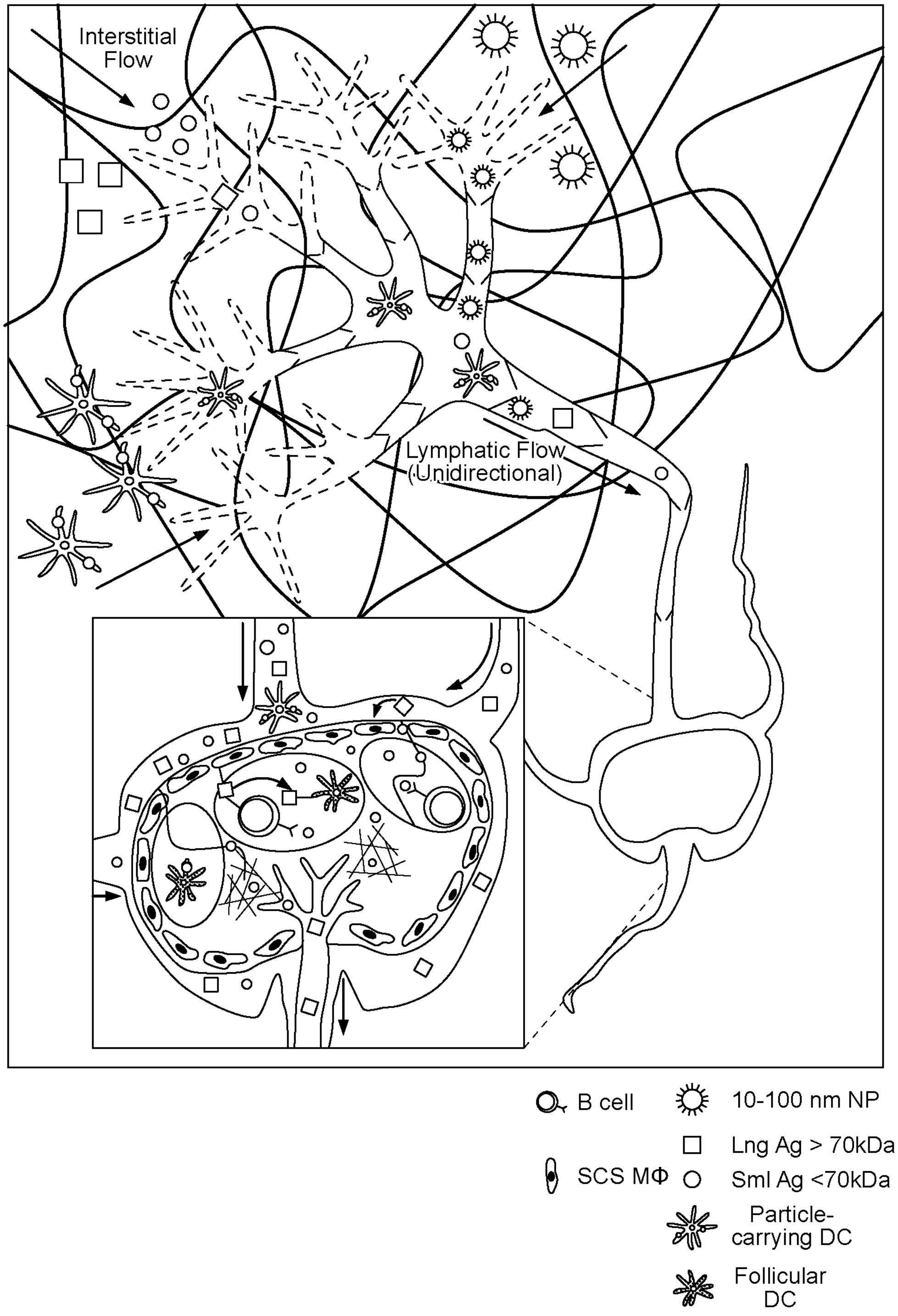
FIG. 3 is a cross-sectional schematic of lymphatic drainage of NPs, showing the lymph node including the lymphatic and adaptive immune system and tumor metastasis, and lymph node accumulation of NPs, including interstitial fluid flow and lymphatic drainage, small, stealthy-coated NPs, showing slower lymphatic drainage, less accumulation in lymph node, and longer retention in lymph-node follicle. Stealthy NPs have a size of less than size of less than 100 nm.

FIGS. 2A-2C are schematics of MPLA (2A); the lipopolysaccharide ("LPS") component thereof (2B) and the immune pathway it initiates (2C).

The TLR4 agonist. MPLA (monophosphoryl lipid A) is a derivative of lipid A, commercially available from InvivoGen as a derivative of lipid A from *Salmonella minnesota* R595 lipopolysaccharide (LPS or endotoxin). MPLA from other bacteria is also commercially available.

MPLA is considerably less toxic than UPS while maintaining the immunostimulatory activity. When tested in animal models as a vaccine adjuvant, MPLA induces a strong Th1 response. As an adjuvant, MPLA has been licensed in Europe and the USA for human vaccines. Conventional dendritic cells (cDCs) play a crucial role in processing and presenting antigens to T cells, and these activated cDCs upregulate CD80 and/or CD86 (costimulatory molecules) or MHCII (the major histocompatibility complex class II), which could enhance the interaction between cDCs and T cells.

C. Anti-Melanoma Agents

There are a number of other types of therapeutic agents that can be used to treat the melanomas. These can be administered in the NPs or directly to the patient in conjunction with treatment with the immunostimulatory NPs.

Targeted drugs only target parts of melanoma cells rather than standard chemotherapy drugs, which basically attack any quickly dividing cells. Most targeted drugs are used to treat melanomas that have certain gene changes such as BRAF gene changes. These represent approximately half of most melanomas. Drugs that target the BRAF protein (BRAF inhibitors) or the MEK proteins (MEK inhibitors) do not work on cells without an abnormal BRAF gene. Usually, BRAF and MEK inhibitors are used in combination. BRAF inhibitors include vemurafenib (ZELBORAF®), dabrafenib (TAFINLAR®), and encorafenib (BRAFTOVI®). MEK inhibitors include trametinib (MEKINIST®), cobimetinib (COTELLIC®), and binimetinib (MEKTOVI®). Common side effects include skin thickening, rash, itching, sensitivity to the sun, headache, fever, joint pain, fatigue, hair loss, and nausea. Less common but serious side effects can include heart rhythm problems, liver problems, kidney failure, severe allergic reactions, severe skin or eye problems, bleeding, and increased blood sugar levels.

A small portion of melanomas have changes in the C-KIT gene that help them grow. Some targeted drugs, such as imatinib (GLEEVEC®) and nilotinib (TASIGNA®), can affect cells with changes in C-KIT.

Pembrolizumab (KEYTRUDA) and nivolumab (OPDIVO®) target PD-1, a protein on T cells that normally help keep these cells from attacking other cells in the body. By blocking PD-1, these drugs boost the immune response against melanoma cells. Atezolizumab (TECENTRIQ®) is a drug that targets PD-L1, a protein related to PD-1 that is found on some tumor cells and immune cells. Blocking this protein can help boost the immune response against melanoma cells. Ipilimumab (YERVOY®) is another drug that boosts the immune response, by blocking CTLA-4.

Relatlimab targets LAG-3, another checkpoint protein on certain immune cells that normally helps keep the immune system in check. This drug is given along with the PD-1 inhibitor nivolumab (in a combination known as OPDUALAG®).

In one embodiment, tumor antigen is administered with, or delivered within, the NPs.

Patients can also be treated with conventional chemotherapeutic agents that inhibit proliferation, but these often suppress the immune system. Radiation is another useful adjunct therapy.

III. Methods of Use

Figure 1B:
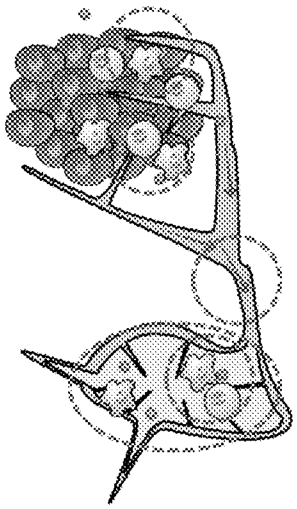
FIG. 1B is a cross-sectional schematic of tumor draining lymph nodes and contralateral lymph node, showing tumor cells, NPs, and immune cells such as dendritic cells.

As shown in FIG. 1, there are a number of sites in the immune system that the NPs can be used to target. Enhancing anti-tumor immunity can be used to activate the overall immune response, change the tumor microenvironment, and enhance T-cell antitumor activity.

NPs drain through the lymph nodes, enhancing delivery to critical immune mediating cells. Lymph nodes play a critical role in the adaptive immune system, as well as in tumor metastasis. The NPs accumulate in the lymph nodes, due to interstitial fluid flow and lymphatic drainage. Based on fluidics and cellular uptake in the lymphatic drainage, NPs less than 100 nm in diameter accumulate faster in the lymph nodes. BNPs having adhesive functional groups on the surface can maintain their binding to the tumor matrix when injected into the tumors while their small size allow them to continuously drain into the lymphatics, with longer retention in lymph-node follicles.

Melanomas are treated by administering the BNPs, or NNPs, although not as preferred, containing an immunostimulant, preferably MPLA. An effective amount can be determined doing routine dose escalation studies based on animal models and comparison with previously utilized dosages of MPLA.

Example 1: Methods of Making MPLA-Loaded PLA-HPG NPs

Materials and Methods

MPLA was dissolved in dimethyl sulfoxide ("DMSO") with triethanolamine ("TEA") (0.2 wt %) at the concentration of MPLA (1 mg/ml). PLA-HPG were dissolved in dichloromethane ("DCM") to 100 mg/ml. For the surfactant-assisted emulsion method, sodium cholate ("CHA") dissolved in distilled water to a concentration of 1 wt % were prepared as a stock solution.

1 ml of HPG-PLA solution (100 mg/ml), 2 ml of MPLA solution (1 mg/ml), and an additional 3 ml of DCM were mixed. To a test tube containing 9 ml of 1 wt % of sodium cholate solution, 6 ml of stock solution with HPG-PLA and MPLA was added dropwise, while the test tube was vortexed, followed by emulsification using a probe sonicator (15 seconds in ice bath, three times).

The emulsion was transferred into a separate beaker containing 21 ml of Sodium cholate solution (1 wt %), and stirred over 3 hours using magnetic stirrer.

Using more DCM than DMSO (preferably greater than 2:1 ratio of DCM/DMSO), within the organic layer, with more water than organic solvent (preferably 3:2 ratio of water/organic solvent) minimizes separate precipitation of MPLA aggregates and improves encapsulation, minimizes vesicles after sonication and results in an inverted NP structure, improving MPLA exposure outward.

To convert BNPs before purification of NPs, NPs (25 mg/ml) were treated with the same volume of NaIO4 (0.1

M) and phosphate buffer (0.1 M, pH 7.4). After incubating in an ice bath for 20 minutes, the same volume of $NaSO_3$ (0.2 M) was added to quench the oxidation reaction, and incubated in an ice bath for 10 minutes. PLA-HPG NPs were washed with filtered centrifugation (100 kDa), three times with distilled water.

Results

Figure 4A:
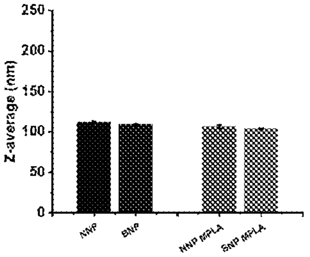
FIGS. 4A-4C are graphs of the properties of PLA NPs, PLA NPs loaded with MPLA, PLA-HPG NPs and PLA-HPG NPs loaded with MPLA. (average diameter, nm, (FIG. 4A); polydispersity index (PDI), (FIG. 4B), and zeta potential (mV), (FIG. 4C)).
Figure 4B:
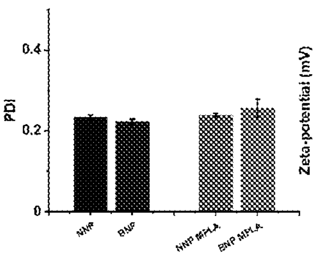
Figure 4C:
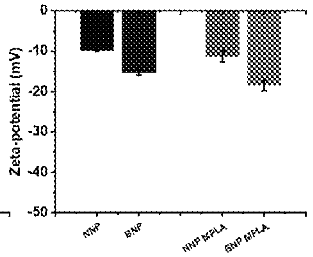

The properties of PLA-HPG NPs (NNP, BNP) and PLA-HPG NPs loaded with MPLA (NNP-MPLA, BNP-MPLA), are shown in FIGS. 4A-4C (average diameter, nm, 4A; polydispersity index (PDI), 4B, and zeta potential (mV), 4C).

Example 2: In Vitro NF-ķB Response of MPLA-Loaded PLA-HPG NPs

Materials and Methods

THP1-DUAL™ cells (INVIVOGEN) derived from human THP-1 monocyte cell lines were used for study of the NF-kB pathway. This cell line has an integration of inducible secreted reporter gene SEAP (secreted embryonic alkaline phosphatase) as the THP1-Dual cells induce activation of NF-kB in response to certain TLR agonists. SEAP, the reporter protein for NF-κB induction, is measured in the cell culture supernatant using QUANTI-BLue™.

THP1-DUAL™ cells were maintained in a growth medium consisting of RPMI 1640, 2 mM L-glutamine, and 25 mM HEPES, supplemented with 10% fetal bovine serum (HYCLONE), 100 U/mL Normocin (INVIVOGEN), and 50 U/mL PenStrep (GIBCO) to between a density of $7\times10^5$ and $2\times10^6$ cells/ml. Initial culture of THP-1 cells was performed in growth medium containing 20% heat inactivated fetal bovine serum (FBS). After the first thaw cycle and two passages, subcultures of the cells were maintained in growth medium. For selection pressure, 10 μg/ml of blasticidin and 100 μg/ml of Zeocin were added to the medium every other passage and cells were passaged every 3 days to maintain an appropriate density. THP1 cells plated into a 96-well plate at a density of around 100,000 cells per well at 180 μl.

They were treated with 20 μl of sample per well of positive control (LPS), free MPLA, BNP-MPLA, NNP-MPLA, blank BNP, and blank NNP at concentrations of MPLA in the particles starting at 2000 ng and halved until 0.488 ng for the MPLA formulations and 500 ng down to 0.244 ng for LPS. Blank particles were added to the same concentration 100,000 ng (same particle concentration given 2% encapsulation rate of MPLA into particles) down to 12 ng.

After 24 hours of induction, SEAP activity was evaluated with the QUANTI-Blue solution. QUANTI-Blue™ is a colorimetric enzyme assay developed to determine any alkaline phosphatase activity (AP) in a biological sample, such as supernatants of cell cultures. QUANTI-Blue™ Solution changes from pink to a purple-blue color in the presence of AP. In a separate, sterile bottle, QUANTI-BLUE solution was prepared by adding 1 ml of QB reagent and 1 ml of QB buffer to 98 ml of sterile water. This was mixed by vortexing and incubating at room temperature for 10 minutes before use. In a separate, flat-bottom 96 well plate, 180 ul of QUANTI-BLUE solution was added per well. Then 20 μl of the sample supernatant was added into the 96 well plate. This plate was incubated at 37° C. for 2 hours. The optical density (OD) was measured after incubation at 620-655 nm using a microplate reader. Triplicate readings were taken for each of the wells.

Results

Figure 5A:
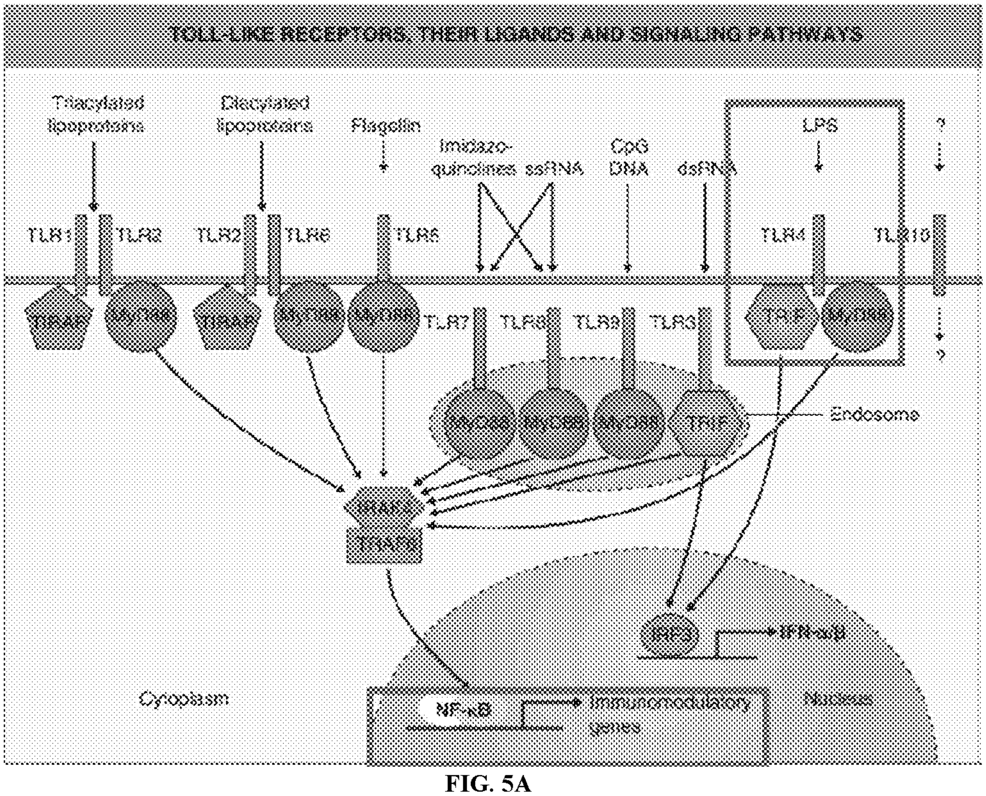
FIG. 5A is a schematic of the NF-ķB response (from Dermatology 4th edition, 192, 202-208 (2014).
Figure 5C:
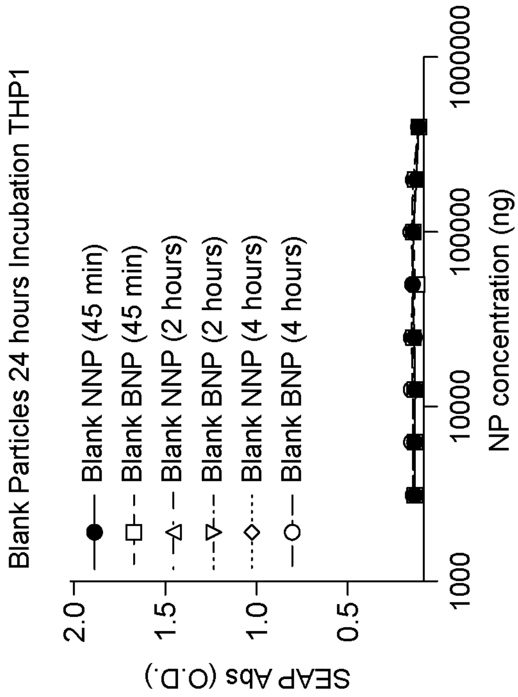
FIGS. 5B and 5C are graphs of the SEAP absorbance of MPLA-loaded PLA-HPG NPs, comparing the effect of treatment with free MPLA, BNP-MPLA, blank BNP, and blank NNP, following 24 hours of induction, evaluating SEAP activity using the NF-ķB-SEAP reporter to determine the effect on TLR-4 signaling in vitro (FIG. 5B) compared to blank controls (FIG. 5C).
Figure 5B:
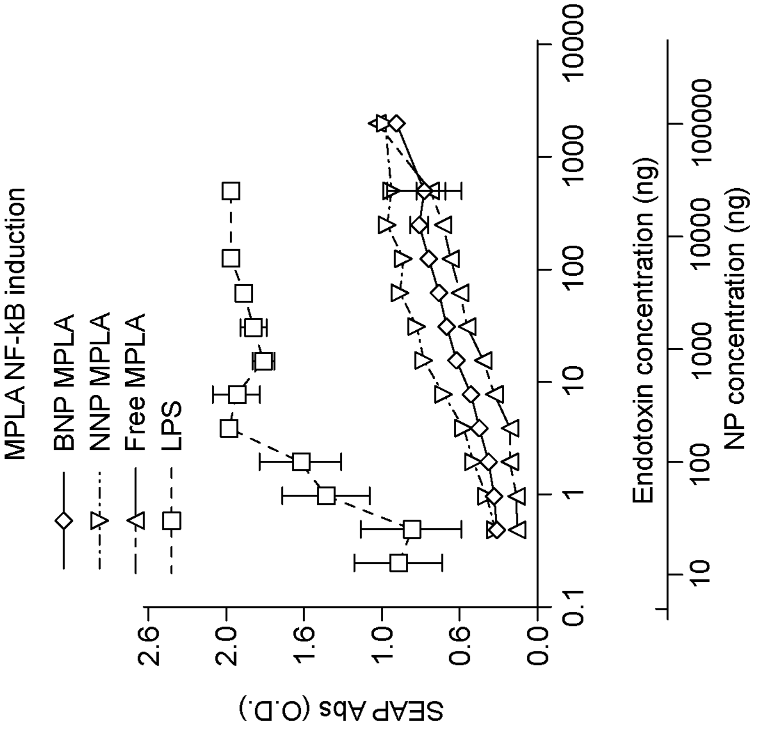

FIG. 5A is a schematic of the Toll Like Receptor pathway and how it triggers the NF-ķB pathway (from Dermatology $4^{th}$ edition, 192, 202-208 (2014). FIGS. 5B and 5C are graphs of the SEAP absorbance of MPLA-loaded PLA-HPG NPs, comparing the effect of treatment with free MPLA, BNP-MPLA, blank BNP, and blank NNP, following 24 hours of induction, evaluating SEAP activity using the NF-ķB-SEAP reporter to determine the effect of TLR-4 signaling in vitro (5B) compared to blank controls (5C).

Example 3: Dendritic Cell Maturation with BNP-MPLA In Vitro

Materials and Methods

Bone marrow derived dendritic cells (BMDC) were obtained from mice. Mice were of 6-8 weeks of age were sacrificed and their bilateral femur and tibia were dissected out. In a petri dish with 70% ethanol, cleaned bones were dipped for sterilization of the exteriors. In a laminar flow hood, both ends of the bone were cut with sterile scissors. A sterilized 1.6 mL Eppendorf tube was prepared and stacked. The top Eppendorf tube were punctured with a sterilized 16G needle to create a hole on the bottom of the tube and the bottom tube was kept opened. The dissected and cleaned femur and tibia were placed on top of the tube and 500 μL of sterile PBS were placed. The stacked tubes with the femur and tibia were centrifuged at 5000 g for one minute. The bottom tube with the supernatant and PBS were collected. The PBS was aspirated without disturbing the pellet. The collected marrow cells were washed with 1 mL of PBS and the cells were resuspended. The cells were centrifuged again at 500 g for five minutes. The collected bone marrow (BM) cells were pipetted into a culture dish with ice cold RPMI complete (CRPMI) media. The cells were counted using a hemocytometer and trypan blue. The cells were then diluted into 10 mL of CRPMI and 20 ng/mL of GM-CSF and plated into petri dishes at a density of $2*10^6$ cells per plate. The cells were incubated and supplemented with 10 mL of CRPMI and 20 ng/mL of GM-CSF at day 3. On day 6 and day 9 after BMDC removal, half of the media was removed and centrifuged. The media was aspirated, and the cells were resuspended in fresh CRPMI and 20 ng/mL GM-CSF. BMDCs were harvested on either day 8, 9, or 10 and plated into a 24 well plate at a density of $1*10^6$ cells per well. They were then incubated with negative control (PBS), positive control (LPS) at 50 ng, free MPLA at 50 ng and 500 ng, free MPLA with blank NNP, free MPLA with blank BNP, NNP-MPLA at 50 ng and 500 ng, and BNP-MPLA at 50 ng and 500 ng.

24 hours and 48 hours after incubation, the BMDCs were collected, gently rinsed with PBS, and resuspended. The culture supernatants were collected separately and stored in −80° C. for evaluation of cytokine response using ELISA later. The cells were rinsed for staining for live cells with Zombie UV followed by surface staining for surface markers including CD11c, MHCII, CD80, and CD86. The cell surface marker expression was measured on a flow cytometer (CYTOFLEX®, Beckman Coulter). The percentage of CD80+ and CD86+ cells (surface markers CD80 and CD86 on dendritic cells are biomarkers for activated dendritic cells in circulation) in CD11c+ and MHC II+ cells (both are surface markers expressed dendritic cells, and macrophages which are antigen presenting cells, APCs, which are important in initiating immune responses used as a marker for dendritic cells isolated from hone marrow cells) from mouse bone marrow derived dendritic cells incubated 24 hours with PBS (control), LPS, MPLA, NNP-MPLA, BNP-MPLA, blank NNP, blank BNP, MPLA plus blank NNP, and MPLA plus blank BNP, was determined.

The proinflammatory cytokine response from the culture supernatant of the incubated bone marrow-derived dendritic cells was also measured, using the TNF-α level measured on enzyme-linked immunosorbent assay (ELISA). LEGEND MAX' mouse TNF-α ELISA kit were used following the protocol from the manufacturer. Briefly, culture supernatant was four-fold diluted with assay diluent, and 100 μl of diluted samples were added to pre-coated plates with TNF-α capture antibodies incubated at room temperature on a plate shaker (150 rpm).

After 2 hours, the plate was washed 5 times. 100 μl of detection antibodies solution were added to each well and incubated for 1 hour. The plates were washed again, followed by addition of avidin-horse radish peroxidase (HRP). After 30 minutes, the plates washed again and 100 μl of substrate solution containing Tetramethyl benzidine was added and the reaction was quenched with stop solution. Absorbance at 450 nm wavelength was measured with a plate reader, and the level of TNF-α calculated with standard curve obtained with serially diluted TNF-α standards.

Results

Figure 6A:
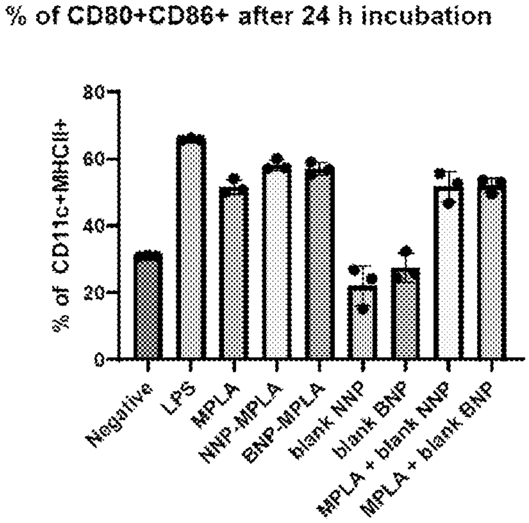
FIGS. 6A and 6B are graphs of the percentage of CD80+ and CD86+ cells (used as markers of maturation of dendritic cells) after 24 and 72 hours incubation, measured from mouse bone marrow derived cells with positive surface markers of CD11c and $MHCII^+$, with control, LPS, MPLA, NNP-MPLA, BNP-MPLA, blank NNP, blank BNP, MPLA plus blank NNP, and MPLA plus blank BNP.
Figure 6B:
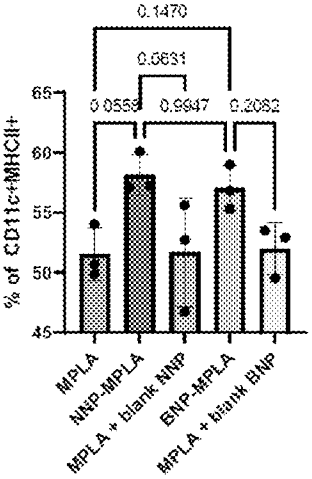

FIGS. 6A and 6B are graphs of the % of CD80+CD86+ from mouse bone marrow derived cells expressing CD11c+ MHCII+ (bone marrow derived dendritic cells, BMDC) for each of the treatment and control groups. The results show that NNP-MPLA and BNP-MPLA yielded higher percentages of CD11c and MHCII+ cells. At 48 hours after incubation of the BMDCs with the particles, BNP-MPLAs induced a higher percentage maturation of dendritic cells compared to the MPLA and NNP-MPLA.

Figure 7A:
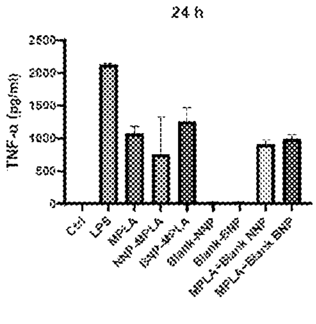
FIGS. 7A-7C are graphs of the levels of TNF-alpha (pg/ml) in the supernatant of bone marrow derived dendritic cells, BMDC, following treatment for 24 hours (FIG. 7A) or 48 hours (FIG. 7B) with control, LPS, MPLA, NNP-MPLA, BNP-MPLA, blank NNP, blank BNP, MPLA plus blank NNP, and MPLA plus blank BNP.
Figure 7B:
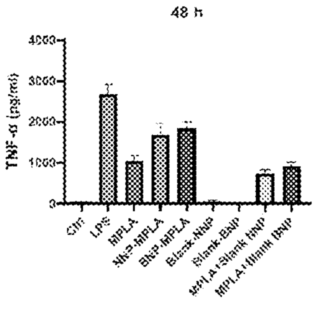
Figure 7C:
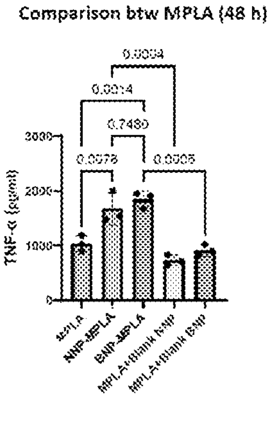

Results are shown in FIGS. 7A-7C for production of bone marrow derived dendritic cells (BMDC), measured as the amount of tumor necrosis factor-alpha (TNF-α) in cell supernatant. FIGS. 7A-7C are graphs of the levels of TNF-alpha (pg/ml) in the supernatant of bone marrow derived dendritic cells, BMDC, following treatment for 24 hours (7A) or 48 hours (7B) with control, LPS, MPLA, NNP-MPLA, BNP-MPLA, blank NNP, blank BNP, MPLA plus blank NNP, and MPLA plus blank BNP, FIG. 7C is a comparison with MPLA after 48 hours of treatment. The NNP-MPLA and BMP-MPLA produced the greatest levels of cytokine relative to MPLA alone or MPLA with blank NNP or blank BNP.

Example 4: Lymphatic Accumulation of NPs in Mice

Materials and Methods

Immunocompetent mice were injected with Yale University Mouse Melanoma Exposed to Radiation 1.7 (YUMMER1.7) cells for in vivo modeling of immunogenic, cutaneous melanoma. The mice were inoculated with 300,000 cells on the left flank and tumors were grown for 8 days without treatment until the tumor volumes (as measured by $W^2*L/2$) reached 40-90 $mm^3$. Mice were randomly assigned to groups (n=5) based on tumor size matching and were injected intratumorally with Cy5 dye loaded nanoparticles, Cy5-NNP and Cy5-BNP) at 10 μl of 50 mg/ml nanoparticles with 10 wt % Cy5-PLA loading, or 0.5 wt % of Cy5 loading. The mice were measured daily to track fluorescence with in vivo imaging using IVIS.

On day seven, the mice were sacrificed and their tumor draining lymph node (TDLN) and contralateral, non-tumor draining lymph nodes (Non-TDLN) were harvested. The ex vivo images of these lymph nodes were collected using IVIS (excitation filter 640 nm, emission filter 680 nm), and the total radiant efficiency were calculated using Live Imaging software.

Results

Figure 8A:
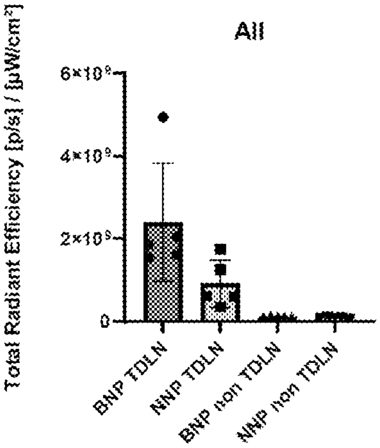
FIGS. 8A-8C are graphs of total radiant efficiency [p/s]/[$\mu W/cm^2$] of BNPs and NNPs in tumor draining lymph nodes (TDLN), both axillary and inguinal, showing BNPs accumulate more than NNPs in all lymph nodes (FIG. 8A), BNPs accumulate more in TDLNs (FIG. 8B) and in non-TDLN (FIG. 8C).
Figure 8B:
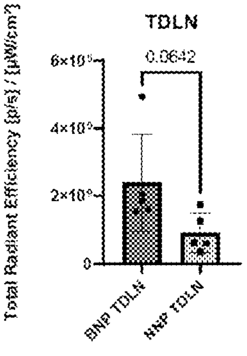
Figure 8C:
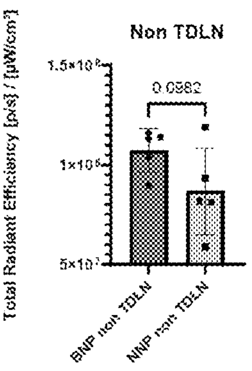

The results are shown in FIGS. 8A-8C. These show that BNP and NNP NPs do not accumulate to the same degree in the same lymph nodes. BNPs accumulate more than NNPs in the lymph nodes (8A). BNPs accumulate more in TDLNs (8B) and in non-TDLNs (8C).

Example 5: Maturation of Dendritic Cells in Mice

Materials and Methods

Immunocompetent mice were injected with Yale University Mouse Melanoma Exposed to Radiation 1.7 (YUMMER1.7) cells for in vivo modeling of immunogenic, cutaneous melanoma. 300,000 cells of YUMMER 1.7 melanoma cells in 50 μL of sterile PBS were intradermally injected into the left flank of syngeneic C57Bl/6 mice.

The mice were watched for tumor growth for eight days until the mice were randomly divided into groups (n=10) based on tumor sizes between 40-90 $mm^3$. The mice received vehicle (10 μl distilled water), free MPLA (10 μg), NNP-MPLA (10 μg of active MPLA), and BNP-MPLA (10 μg of active MPLA) intratumorally. The mice were sacrificed either at 24 hours or 72 hours after the single intratumoral injection. The tumor draining lymph nodes, both axillary and inguinal, were collected from each mouse. A petri dish was used to collect the lymph nodes, and the frosted ends of microscope slides were used to gently release immune cells from the lymph nodes into fresh CRPMI and placed on ice until resuspension. The collected cells were then resuspended through a 70 μm mesh into a new collection tube with CRPMI and kept on ice.

After lymph node single cell collection, the cells were rinsed with sterile PBS and plated into a 96 round-bottom well plate at a concentration density of $1\text{-}2\times10^6$ cells per well then rinsed again with PBS. The cells were stained with live/dead stain followed by nonspecific surface binding blocking, and then by surface marker stains including CD3, CD4, CD8, CD11c, CD80, and CD86 to assess dendritic cell maturation. The stained cells were then detected by flow cytometer (Cytoflex, Beckman Coulter). The dendritic cells were defined as cells that were CD3−CD11c+ and then matured dendritic cells were defined as cells expressing the aforementioned markers in addition to CD80+ and CD86+.

Results

Figure 9A:
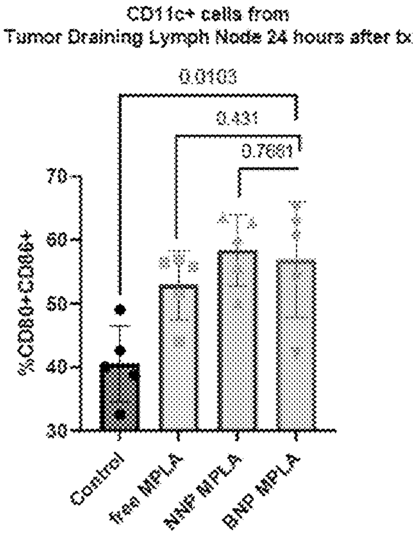
FIGS. 9A and 9B are graphs of the % of CD80+CD86+ cells in CD11c+ cells in the TDLNs, including both axillary and inguinal, 24 hours (FIG. 9A) or 72 hours (FIG. 9B) following in-vivo intratumoral injection with vehicle (water), MPLA (10 ug), NNP-MPLA (10 ug), and BNP-MPLA (10 ug). Mice were injected with melanoma cells 8 days before these injections and were sized matched for each group.
Figure 9B:
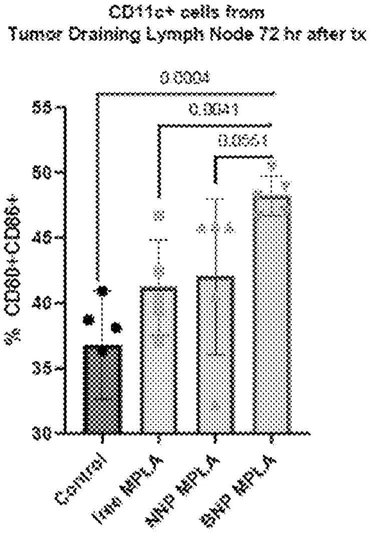
Figure 10A:
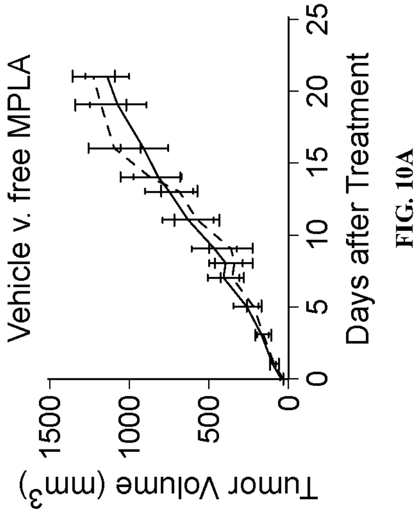
FIGS. 10A-10E are graphs of in-vivo melanoma tumor volume ($mm^3$) days after treatment for vehicle versus free MPLA (FIG. 10A); vehicle versus BNP-MPLA (FIG. 10B), Vehicle (FIG. 10C), free MPLA (FIG. 10D) and BNP-MPLA (FIG. 10E). Mice were injected with melanoma cells 8 days before treatment injections.
Figure 10B:
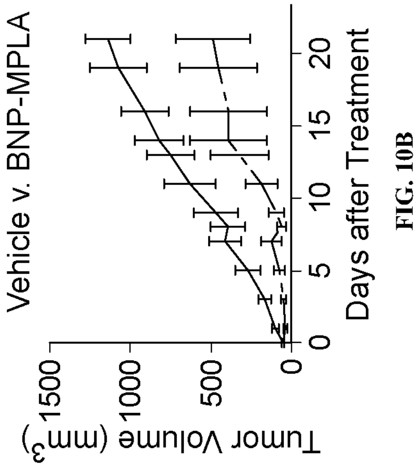
Figure 10C:
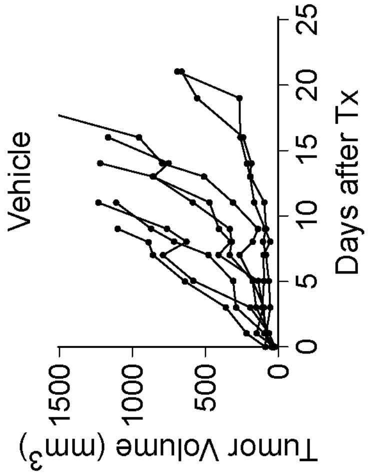
Figure 10D:
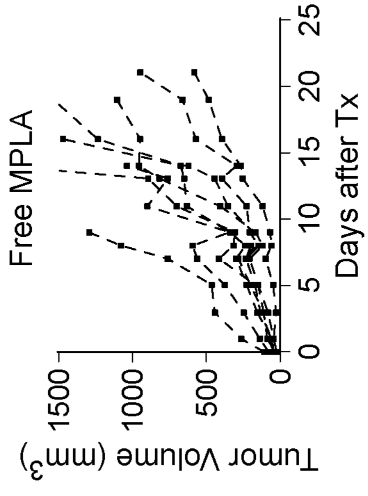
Figure 10E:
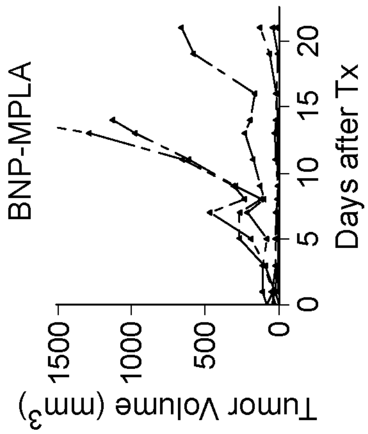

FIGS. 9A and 9B are graphs of the % of mature dendritic cells as defined by CD80+CD86+ surface markers on cells that expressed CD11c+. At the 24 hour time point after intratumoral injection, there was significant increase in dendritic cell maturation by free MPLA, NNP-MPLA, and BNP-MPLA. However, at 72 hour time point there is statistically significant increase in matured dendritic cells in the TDLN from mice injected with BNP-MPLA compared to free MPLA and greater than mice injected with NNP-MPLA. This showed that BNP MPLA produced the high levels of mature dendritic cells in the draining lymph nodes and also demonstrated prolonged levels of mature dendritic cells in the lymph nodes.

Example 6: Treatment to Tumors with BNP-MPLA

Materials and Methods

Immunocompetent mice were injected with Yale University Mouse Melanoma Exposed to Radiation 1.7 (YUM- MER1.7) cells for in vivo modeling of immunogenic, cutaneous melanoma. 300,000 cells of YUMMER 1.7 melanoma cells in 50 μL of sterile PBS were intradermally injected into the left flank of syngeneic C57Bl/6 mice. The mice were watched for tumor growth for eight days until the mice were randomly divided into groups (n=8) based on tumor sizes between 40-90 $mm^3$.

Eight mice received vehicle (20 μl distilled water), eight received MPLA (10 μg) in two weekly injections at day 0 and day 7; and BNP-MPLA (10 μg of active MPLA) in two weekly injections on day 0 and day 7. The mice tumor sizes were measured every two to three days with volume defined as $W^2*L/2$. The mice were sacrificed when the tumors reached a size of 1 $cm^3$. The tumor growth was watched until day 60 after the first treatment.

Results

FIGS. 10A-10E are graphs of tumor volume ($mm^3$) days after treatment for vehicle versus free MPLA (10A); vehicle versus BNP-MPLA (10B), Vehicle (10C), free MPLA (10D) and BNP-MPLA (10E).

Figure 11:
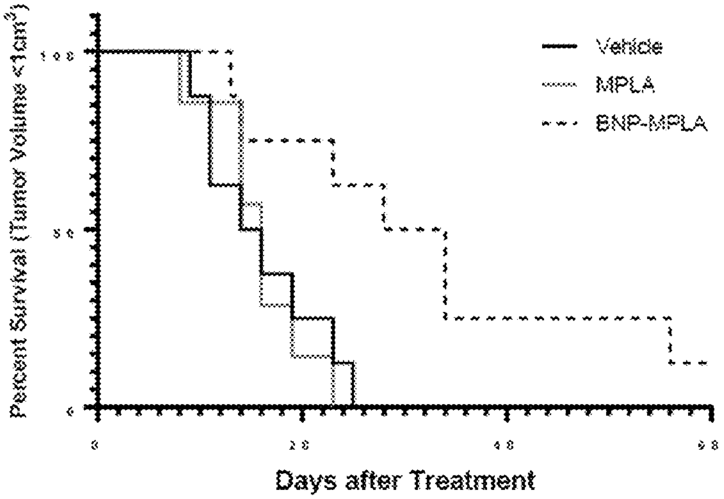
FIG. 11 is a graph of the percent survival (defined as tumor volume less than 1 $cm^3$) versus days of treatment for vehicle, MPLA and BNP-MPLA.

FIG. 11 is a graph of the percent survival (tumor volume less than 1 $cm^3$) versus days of treatment, for vehicle, MPLA and BNP-MPLA.

The results demonstrate a statistically significant decrease in tumor volume and prolonged survival for mice with cutaneous melanoma treated with BNP-MPLA.

Example 7: Treatment of Tumors in Mice and Comparison of Survival, Weight Change and Immune Cell Activation for Free MPLA, NNP-MPLA, Alone or in Combination with Chemotherapeutic

Materials and Methods

Studies were conducted to determine activation of immune cells in vivo in tumor draining lymph nodes (TDLNs) comparing control (saline), with free MPLA, NNP-MPLA, and BNP-MPLA.

CD80 and CD86 expression in live CD11c+ cells in TDLNs after a single intratumoral injection at 24 h was measured in live CD11c+ cells in non-TDLNs after a single injection at 24 h. Corresponding quantification of BMDCs maturation in non-TDLN was also measured.

Activation of BMDCs in TDLNs after 72 h after a single injection was assessed.

Studies were conducted to determine if NP encapsulation of MPLA increased M1 macrophage population in TDLN. Measurements of CD68+ cells were made 72 h and 5 days after a single injection.

Studies were conducted to determine if nanoparticle encapsulation enhances the immunostimulatory potency of MPLA and remodels the tumor microenvironment. YUMMER1.7 melanoma tumors were used to evaluate the changes in tumor microenvironment after an injection of control (water), free MPLA, and NNP MPLA. The tumors were size matched and treated on day 8 after the tumor inoculation. 72 hours after a single injection with the treatment, the tumors were harvested for analysis with flow cytometry. The number of natural killer T cells, Treg cells, and CD45+CD3+ cells in the tumors with mice injected with NNP-MPLA was quantified. injection was analyzed. Cytokine (interferon gamma) levels were also determined.

A murine melanoma was treated with intratumoral NNP-MPLA or free MPLA in comparison to and in conjunction with an investigational chemotherapy SBI-111 at a determined low dose. It was important to use lowest possible dose of chemotherapy given the cytotoxic drugs may hinder immunomodulatory effects given its cytotoxicity against all cells including immune cells. Using YUMMER1.7 melanoma tumors, the treatment was administered only once, including control, NNP-MPLA, SBI-111, and combination. Tumor growth and survival was determined. Weight of animals was also measured.

YUMMER1.7 melanoma tumors were treated with i.t. injections of control (distilled water), free MPLA, NNP-MPLA, combination SBI-111 and MPLA, and combination SBI-111 and NNP-MPLA. Growth of tumors, weight of treated animals, and survival of animals injected with a single treatment of free MPLA, NNP-MPLA, SBI-111, or combination chemoimmunotherapy with free MPLA or NNP-MPLA was assessed.

Results

FIGS. 12A-12C are graphs showing the amount of activation of immune cells in vivo in tumor draining lymph nodes (TDLNs) with MPLA is increased with nanoparticle encapsulation. In both the TDLN and non-TDLN, there is a significant dendritic cell maturation in vivo with NNP or BNP-MPLA compared to the free MPLA.

Figure 13A:
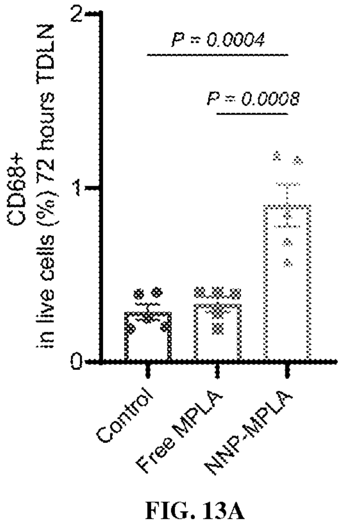
FIGS. 13A and 13B show the increased M1 macrophage population in TDLN with NP encapsulation of MPLA, at 72 h and 5 days after a single injection.
Figure 13B:
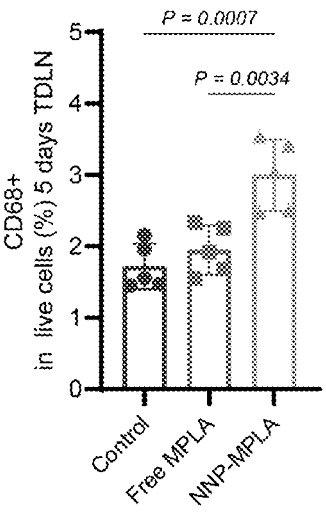
Figure 14A:
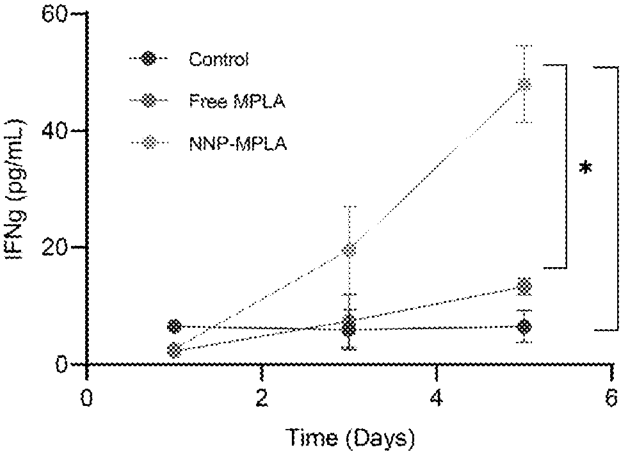
FIGS. 14A-14D show that nanoparticle encapsulation enhances the immunostimulatory potency of MPLA and remodels the tumor microenvironment. YUMMER1.7 melanoma tumors were used to evaluate the changes in tumor microenvironment after an injection of control (water), free MPLA, and NNP MPLA. The tumors were size matched and treated on day 8 after the tumor inoculation. 72 hours after a single injection with the treatment, the tumors were harvested for analysis with flow cytometry. In the tumors, there was a significantly increased population of natural killer T cells in the tumors with mice injected with NNP-MPLA.
Figure 14B:
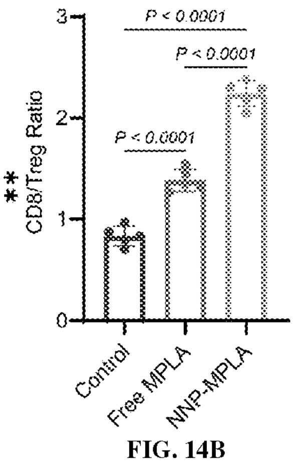
Figure 14C:
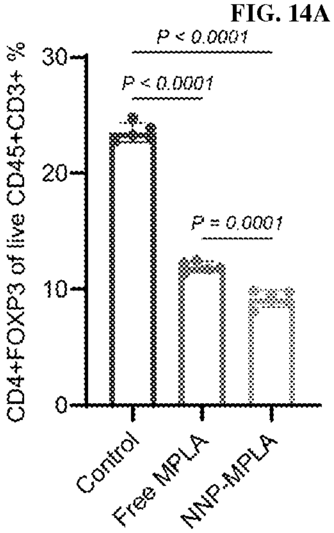
Figure 14D:
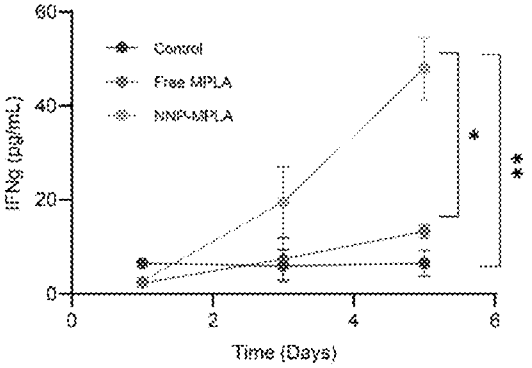

FIG. 12C shows results for activation of BMDCs in TDLNs after 72 h after a single injection, demonstrating that NNP-MPLA prolongs the dendritic cell maturation compared to free MPLA FIGS. 13A and 13B show the increased M1 macrophage population in TDLN with NP encapsulation of MPLA, at 72 h and 5 days after a single injection. FIG. 13A show corresponding quantification of CD68+ cells in TDLN 72 h after injection. FIG. 13B show corresponding quantification of CD68+ cells in TDLN 5 days after injection.

FIGS. 14A-14D show that nanoparticle encapsulation enhances the immunostimulatory potency of MPLA and remodels the tumor microenvironment. YUMMER1.7 melanoma tumors were used to evaluate the changes in tumor microenvironment after an injection of control (water), free MPLA, and NNP MPLA.

There was a significantly increased population of natural killer T cells in the tumors with mice injected with NNP-MPLA with significantly decreased Treg population in NNP-MPLA treated tumors in comparison to the control and free MPLA.

There was a significantly increased CD8 to Treg ratio in tumors treated with NNP-MPLA indicating a higher cytotoxic T cell population with NNP-MPLA treatment compared to both control and free MPLA.

There was a notable increase in cytokine production in the NNP-MPLA treated groups; at 24 hr, the detectable IFN-γ were similar across groups, however there was a sustained increase in IFN-γ detected in serum in NNP-MPLA injected mice after 72 hr, and significantly increased IFN-γ at 5 days after NNP-MPLA injection compared to control and free MPLA.

Figure 15A:
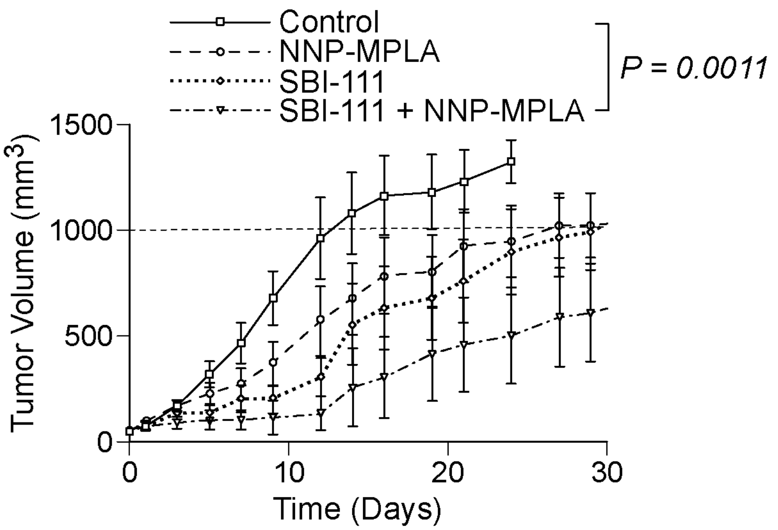
FIGS. 15A-15C show that treatment of murine melanoma with intratumoral NNP-MPLA is superior to free MPLA, The effect of NNP-MPLA was assessed in comparison to and in conjunction with an investigational chemotherapy SBI-111 at a determined low dose.
Figure 15B:
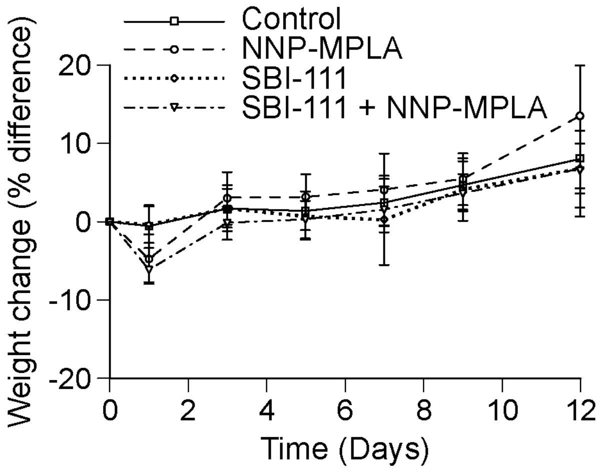
Figure 15C:
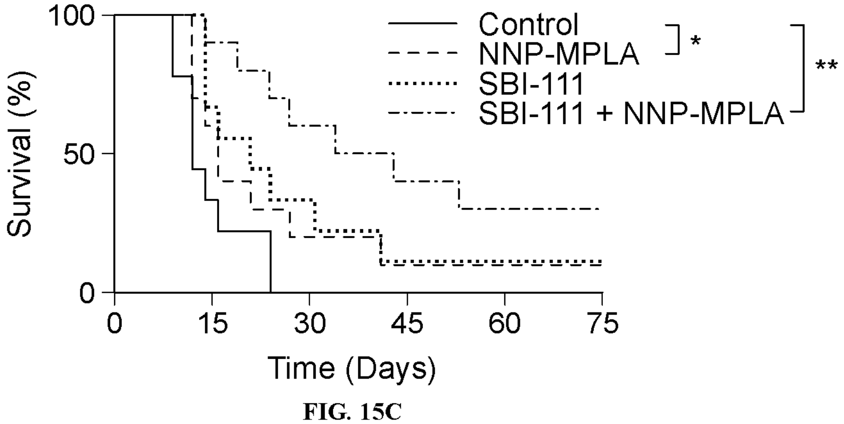

FIGS. 15A-15C show that treatment of murine melanoma with intratumoral NNP-MPLA is superior to free MPLA.

The effect of NNP-MPLA was assessed in comparison to and in conjunction with an investigational chemotherapy SBI-111 at a determined low dose.

FIG. 15A shows there was a significant delay in tumor growth with both NNP-MPLA and chemotherapy SBI-111.

A single treatment and the combination treatment was well tolerated in mice as evidenced by only a slight weight change of mice on the day after treatment.

FIG. 15D shows the survival curve of mice after a single treatment with either NNP-MPLA, SBI-111, or SBI-111 and NNP-MPLA. Survival was significantly increased with treatment, with greatest survival with the combination of SBI-111 and NNP-MPLA.

Figure 16B:
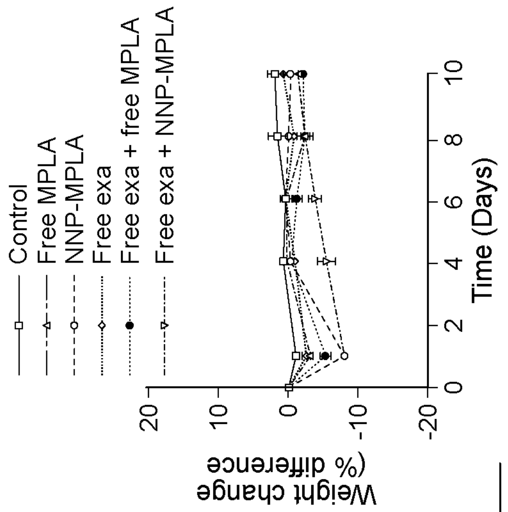
FIGS. 16A-16C show results of treatment of murine melanoma with combination chemoimmunotherapy with NNP-MPLA. YUMMER1.7 melanoma tumors were treated with i.t. injections of control (distilled water), free MPLA, NNP-MPLA, combination SBI-111 and MPLA, and combination SBI-111 and NNP-MPLA.
Figure 16C:
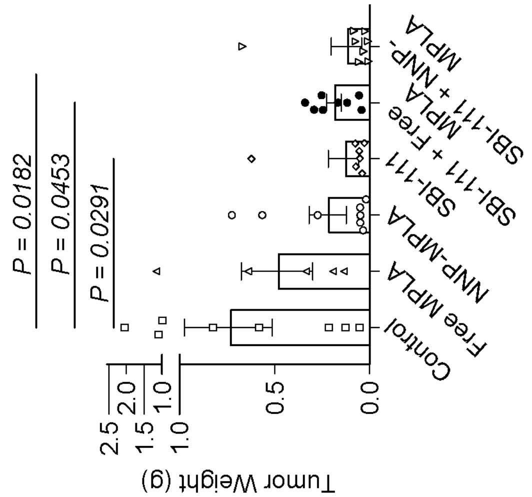
Figure 16A:
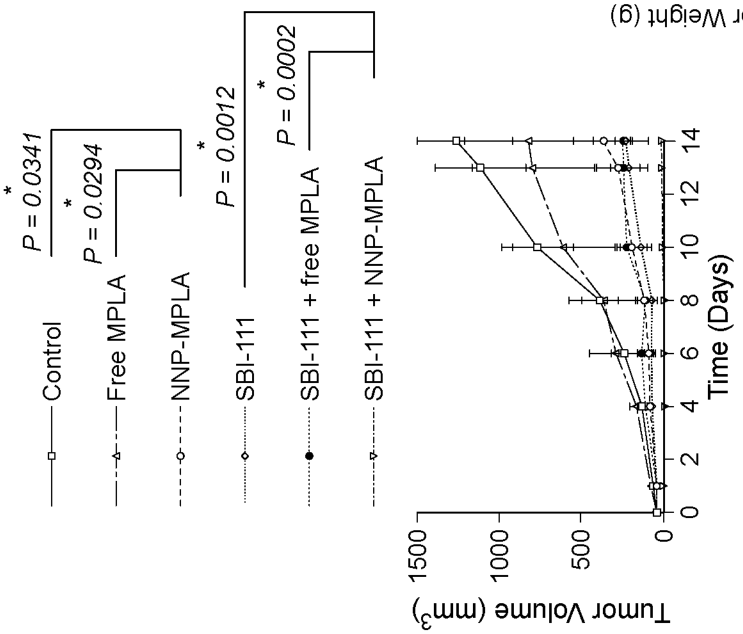

FIGS. 16A-16C show results of treatment of murine melanoma with combination chemoimmunotherapy with NNP-MPLA. FIG. 16A shows the combined growth curve for tumors injected with a single treatment of free MPLA, NNP-MPLA, SBI-111, or combination chemoimmunotherapy with free MPLA or NNP-MPLA. FIG. 16B shows the mouse weight changes after treatment injection. FIG. 16C show the tumor weight at harvest, 14 days after single treatment.

The combination of chemotherapy with NNP-MPLA demonstrated a stark slowing in tumor growth.

We claim:

1. A formulation comprising nanoparticles formed of hyperbranched polyglycerol covalently bound to polylactic acid or polyglycolic acid, or a copolymer of lactide and glycolide, presenting the hyperbranched polyglycerol molecules on the surface, and an immunostimulant therein, wherein the immunostimulant is in an amount effective, when administered to a tumor, to stimulate an immune response against the tumor, wherein the immunostimulant is monophosphoryl lipid A, wherein the formulation is in a form suitable for intratumoral injection, and wherein the formulation is in a dosage for intratumoral treatment of melanoma.

2. The formulation of claim 1 in combination with a drug selected from the group consisting of BRAF inhibitors, MEK inhibitors, drugs affecting cells with changes in C-KIT, drugs targeting PD-1, drugs targeting PD-L1, drugs targeting LAG-3, and PD-1 inhibitors.

3. A method of treating skin tumors comprising administering the formulation of claim 1 to an individual in need thereof.

4. The method of claim 3 wherein the skin tumor is melanoma.

5. The formulation of claim 1, wherein the nanoparticles have an average diameter of from about 5 nm to about 100 nm.

6. The formulation of claim 1, wherein one or more surface hydroxyl groups of the hyperbranched polyglycerol are converted to aldehydes, amines, oximes, or O-substituted oximes, or a combination thereof.

7. The formulation of claim 1, wherein one or more surface hydroxyl groups of the hyperbranched polyglycerol are converted to aldehydes.

8. A formulation comprising (a) a first plurality of nanoparticles formed of hyperbranched polyglycerol covalently bound to poly lactic acid or polyglycolic acid, or a copolymer of lactide and glycolide, presenting the hyperbranched polyglycerol molecules on the surface, and a first immunostimulant therein;

and (b) a second plurality of nanoparticles formed of hyperbranched polyglycerol covalently bound to poly lactic acid or polyglycolic acid, or a copolymer of lactide and glycolide, presenting the hyperbranched polyglycerol molecules on the surface, and a second immunostimulant therein, wherein one or more surface hydroxyl groups of the hyperbranched polyglycerol are converted to aldehydes, amines, oximes, or O-substituted oximes, or a combination thereof;

wherein the first and second immunostimulants are in an amount effective, when administered to a skin tumor, to stimulate an immune response against the skin tumor and/or to prolong local antitumor immune response in the skin tumor, wherein the first and second immunostimulants are monophosphoryl lipid A, and wherein the formulation is in a dosage for intratumoral treatment of melanoma.

9. The formulation of claim 1, wherein the nanoparticles are produced by sodium cholate-assisted emulsion.

10. The formulation of claim 8, wherein the formulation is in a form suitable for intratumoral injection.

11. The formulation of claim 8, wherein the one or more surface hydroxyl groups of the hyperbranched polyglycerol are converted to aldehydes.

12. The formulation of claim 8, wherein the first and second plurality of nanoparticles independently have an average diameter of from about 5 nm to about 100 nm.

* * * * *